(12) United States Patent
Tadros

(10) Patent No.: US 7,544,483 B2
(45) Date of Patent: Jun. 9, 2009

(54) METHOD FOR THE PRODUCTION OF PROTAMINE

(76) Inventor: Monier Tadros, Am Retzgraben 58, Freiburg (DE) 79108

( * ) Notice: Subject to any disclaimer, the term of this patent is extended or adjusted under 35 U.S.C. 154(b) by 220 days.

(21) Appl. No.: 10/518,001

(22) PCT Filed: Jun. 14, 2002

(86) PCT No.: PCT/EP02/06596

§ 371 (c)(1),
(2), (4) Date: Aug. 3, 2005

(87) PCT Pub. No.: WO03/106485

PCT Pub. Date: Dec. 24, 2003

(65) Prior Publication Data

US 2006/0062775 A1 Mar. 23, 2006

(51) Int. Cl.
*C12P 21/06* (2006.01)
*C12N 15/00* (2006.01)
*C12N 1/20* (2006.01)
*C07H 21/02* (2006.01)

(52) U.S. Cl. .............. 435/69.1; 435/320.1; 435/252.3; 536/23.1

(58) Field of Classification Search ............ 435/69.1, 435/252.3, 320.1; 536/23.1
See application file for complete search history.

(56) References Cited

U.S. PATENT DOCUMENTS

| | | | |
|---|---|---|---|
| 4,945,050 | A | 7/1990 | Sanford et al. |
| 5,545,817 | A | 8/1996 | McBride et al. |

FOREIGN PATENT DOCUMENTS

| | | |
|---|---|---|
| EP | 0239400 A2 | 9/1987 |
| EP | 0332104 A2 | 9/1989 |
| EP | 0359472 A2 | 3/1990 |
| EP | 0386962 A2 | 9/1990 |
| WO | 90/07861 A1 | 7/1990 |
| WO | 91/16432 A1 | 10/1991 |
| WO | 91/19806 A1 | 12/1991 |
| WO | 94/20627 A1 | 9/1994 |
| WO | 96/06532 A1 | 3/1996 |
| WO | 00/55196 A1 | 9/2000 |

OTHER PUBLICATIONS

McMahon et al., Nature, 364, 346-349, 1993.*
Molecular Cloning: a Laboratory Manual: 2nd edition, Sambrook et al, 1989, Cold Spring Harbor Laboratory Press, pp. 1.7-1.20.
Current Protocols in Molecular Biology, Second Edition, Ausubel et al. eds., John Wiley & Sons, 1992, pp. p. 2-3 to p. 2-22.

* cited by examiner

*Primary Examiner*—Maryam Monshipouri

(57) ABSTRACT

The present invention generally relates to the fields of genetic engineering and biochemistry. In particular, it relates to a novel method for the production of protamine as well as to novel method for the production of protamine as well as to novel compositions containing protamine as active ingredient. Furthermore, it relates to the use of said compositions for killing or inhibiting micobial cells.

43 Claims, 4 Drawing Sheets
(1 of 4 Drawing Sheet(s) Filed in Color)

SEQUENCE LISTING

<160> NUMBER OF SEQ ID NOS: 36

<210> SEQ ID NO 1
<211> LENGTH: 102
<212> TYPE: DNA
<213> ORGANISM: Oncorhynchus mykiss
<220> FEATURE:
<221> NAME/KEY: CDS
<222> LOCATION: (1)..(99)
<220> FEATURE:
<223> OTHER INFORMATION: aa sequence derived from ORF of nucleotide
      sequence

<400> SEQUENCE: 1 atg ccc aga aga cgc aga tcc tcc agc cga cct gtc cgc agg cgc cgc      48
Met Pro Arg Arg Arg Arg Ser Ser Ser Arg Pro Val Arg Arg Arg Arg
 1               5                  10                  15 cgc ccc agg gtg tcc cga cgt cgt cgc agg aga gga ggc cgc agg agg      96
Arg Pro Arg Val Ser Arg Arg Arg Arg Arg Gly Gly Arg Arg Arg
            20                  25                  30 cgt tag                                                             102
Arg

<210> SEQ ID NO 2
<211> LENGTH: 33
<212> TYPE: PRT
<213> ORGANISM: Oncorhynchus mykiss
<220> FEATURE:
<223> OTHER INFORMATION: aa sequence derived from ORF of nucleotide
      sequence

<400> SEQUENCE: 2

Met Pro Arg Arg Arg Arg Ser Ser Ser Arg Pro Val Arg Arg Arg Arg
 1               5                  10                  15

Arg Pro Arg Val Ser Arg Arg Arg Arg Arg Gly Gly Arg Arg Arg
            20                  25                  30

Arg

<210> SEQ ID NO 3
<211> LENGTH: 102
<212> TYPE: DNA
<213> ORGANISM: Oncorhynchus mykiss
<220> FEATURE:
<221> NAME/KEY: CDS
<222> LOCATION: (1)..(99)
<220> FEATURE:
<223> OTHER INFORMATION: aa sequence derived from ORF of nucleotide
      sequence

<400> SEQUENCE: 3 atg ccc aga aga cgc aga tcc tcc aga cca cct gtc cgc agg cgc cgc      48
Met Pro Arg Arg Arg Arg Ser Ser Arg Pro Pro Val Arg Arg Arg
 1               5                  10                  15 cgc ccc agg gtg tcc cga cgt cgt cgc agg aga gga ggc cgc agg agg      96
Arg Pro Arg Val Ser Arg Arg Arg Arg Arg Gly Gly Arg Arg Arg
            20                  25                  30 cgt tag                                                             102
Arg

<210> SEQ ID NO 4
<211> LENGTH: 33
<212> TYPE: PRT
<213> ORGANISM: Oncorhynchus mykiss
<220> FEATURE:

<223> OTHER INFORMATION: aa sequence derived from ORF of nucleotide
      sequence

<400> SEQUENCE: 4

Met Pro Arg Arg Arg Arg Ser Ser Arg Pro Val Arg Arg Arg Arg
 1               5                  10                  15

Arg Pro Arg Val Ser Arg Arg Arg Arg Arg Gly Gly Arg Arg Arg
                20                  25                  30

Arg

<210> SEQ ID NO 5
<211> LENGTH: 102
<212> TYPE: DNA
<213> ORGANISM: Oncorhynchus mykiss
<220> FEATURE:
<221> NAME/KEY: CDS
<222> LOCATION: (1)..(99)
<220> FEATURE:
<223> OTHER INFORMATION: aa sequence derived from ORF of nucleotide
      sequence

<400> SEQUENCE: 5 atg ccc aga aga cgc aga tcc tcc aga cga cct gtc cgc agg cgc cgc       48
Met Pro Arg Arg Arg Arg Ser Ser Arg Arg Pro Val Arg Arg Arg Arg
 1               5                  10                  15 cgc ccc agg gtg tcc cga cgt cgt cgc agg aga gga ggc cgc agg agg       96
Arg Pro Arg Val Ser Arg Arg Arg Arg Arg Gly Gly Arg Arg Arg
                20                  25                  30 cgt tag                                                              102
Arg

<210> SEQ ID NO 6
<211> LENGTH: 33
<212> TYPE: PRT
<213> ORGANISM: Oncorhynchus mykiss
<220> FEATURE:
<223> OTHER INFORMATION: aa sequence derived from ORF of nucleotide
      sequence

<400> SEQUENCE: 6

Met Pro Arg Arg Arg Arg Ser Ser Arg Arg Pro Val Arg Arg Arg Arg
 1               5                  10                  15

Arg Pro Arg Val Ser Arg Arg Arg Arg Arg Gly Gly Arg Arg Arg
                20                  25                  30

Arg

<210> SEQ ID NO 7
<211> LENGTH: 102
<212> TYPE: DNA
<213> ORGANISM: Oncorhynchus mykiss
<220> FEATURE:
<221> NAME/KEY: CDS
<222> LOCATION: (1)..(99)
<220> FEATURE:
<223> OTHER INFORMATION: aa sequence derived from ORF of nucleotide
      sequence

<400> SEQUENCE: 7 atg ccc aga aga cgc aga tcc tct agc cga cct gtc cgc agg cgc cgc       48
Met Pro Arg Arg Arg Arg Ser Ser Ser Arg Pro Val Arg Arg Arg Arg
 1               5                  10                  15 cgc gcc agg gtg tcc cga cgt cgt cgc agg aga gga cgc cgc agg agg       96
Arg Ala Arg Val Ser Arg Arg Arg Arg Arg Gly Arg Arg Arg
                20                  25                  30

```
cgt tag                                                          102
Arg

<210> SEQ ID NO 8
<211> LENGTH: 33
<212> TYPE: PRT
<213> ORGANISM: Oncorhynchus mykiss
<220> FEATURE:
<223> OTHER INFORMATION: aa sequence derived from ORF of nucleotide
      sequence

<400> SEQUENCE: 8

Met Pro Arg Arg Arg Arg Ser Ser Ser Arg Pro Val Arg Arg Arg
 1               5                  10                  15

Arg Ala Arg Val Ser Arg Arg Arg Arg Arg Gly Arg Arg Arg Arg
                20                  25                  30

Arg

<210> SEQ ID NO 9
<211> LENGTH: 102
<212> TYPE: DNA
<213> ORGANISM: Oncorhynchus mykiss
<220> FEATURE:
<221> NAME/KEY: CDS
<222> LOCATION: (1)..(99)
<220> FEATURE:
<223> OTHER INFORMATION: aa sequence derived from ORF of nucleotide
      sequence

<400> SEQUENCE: 9 atg ccc aga aga cgc aga tcc tcc agc cga cct gtc cgc agg cgc cgc    48
Met Pro Arg Arg Arg Arg Ser Ser Ser Arg Pro Val Arg Arg Arg
 1               5                  10                  15 cgc ccc agg gtg tcc cga cgt cgt cgc agg aga gga cgc cgc agg agg    96
Arg Pro Arg Val Ser Arg Arg Arg Arg Arg Gly Arg Arg Arg Arg
                20                  25                  30 cgt tag                                                          102
Arg

<210> SEQ ID NO 10
<211> LENGTH: 33
<212> TYPE: PRT
<213> ORGANISM: Oncorhynchus mykiss
<220> FEATURE:
<223> OTHER INFORMATION: aa sequence derived from ORF of nucleotide
      sequence

<400> SEQUENCE: 10

Met Pro Arg Arg Arg Arg Ser Ser Ser Arg Pro Val Arg Arg Arg
 1               5                  10                  15

Arg Pro Arg Val Ser Arg Arg Arg Arg Arg Gly Arg Arg Arg Arg
                20                  25                  30

Arg

<210> SEQ ID NO 11
<211> LENGTH: 102
<212> TYPE: DNA
<213> ORGANISM: Oncorhynchus keta
<220> FEATURE:
<221> NAME/KEY: CDS
<222> LOCATION: (1)..(99)
<220> FEATURE:
<223> OTHER INFORMATION: aa sequence derived from ORF of nucleotide
      sequence

<400> SEQUENCE: 11
```

```
atg ccc aga aga cgc aga tcc tcc agc cga cct gtc cgc agg cgc cgc      48
Met Pro Arg Arg Arg Arg Ser Ser Ser Arg Pro Val Arg Arg Arg Arg
 1               5                  10                  15 cgc cct agg gtg tcc cga cgt cgt cgc agg aga gga ggc cgc agg agg      96
Arg Pro Arg Val Ser Arg Arg Arg Arg Arg Gly Gly Arg Arg Arg
            20                  25                  30 cgt tag                                                             102
Arg
```

<210> SEQ ID NO 12
<211> LENGTH: 33
<212> TYPE: PRT
<213> ORGANISM: Oncorhynchus keta
<220> FEATURE:
<223> OTHER INFORMATION: aa sequence derived from ORF of nucleotide
      sequence

<400> SEQUENCE: 12

```
Met Pro Arg Arg Arg Arg Ser Ser Ser Arg Pro Val Arg Arg Arg
 1               5                  10                  15

Arg Pro Arg Val Ser Arg Arg Arg Arg Arg Gly Gly Arg Arg Arg
            20                  25                  30

Arg
```

<210> SEQ ID NO 13
<211> LENGTH: 102
<212> TYPE: DNA
<213> ORGANISM: Oncorhynchus mykiss
<220> FEATURE:
<221> NAME/KEY: CDS
<222> LOCATION: (1)..(99)
<220> FEATURE:
<221> NAME/KEY: misc_feature
<222> LOCATION: (54)..(54)
<223> OTHER INFORMATION: n = a or c or g or t
<220> FEATURE:
<223> OTHER INFORMATION: nucleotide sequence derived from amino acid
      sequence

<400> SEQUENCE: 13

```
atg ccc aga aga cgc aga tcc tcc agc cga cct gtc cgc agg cgc cgc      48
Met Pro Arg Arg Arg Arg Ser Ser Ser Arg Pro Val Arg Arg Arg Arg
 1               5                  10                  15 cgc gcn agg gtg tcc cga cgt cgt cgc agg aga gga ggc cgc agg agg      96
Arg Ala Arg Val Ser Arg Arg Arg Arg Arg Gly Gly Arg Arg Arg
            20                  25                  30 cgt tag                                                             102
Arg
```

<210> SEQ ID NO 14
<211> LENGTH: 33
<212> TYPE: PRT
<213> ORGANISM: Oncorhynchus mykiss
<220> FEATURE:
<223> OTHER INFORMATION: nucleotide sequence derived from amino acid
      sequence

<400> SEQUENCE: 14

```
Met Pro Arg Arg Arg Arg Ser Ser Ser Arg Pro Val Arg Arg Arg Arg
 1               5                  10                  15

Arg Ala Arg Val Ser Arg Arg Arg Arg Arg Gly Gly Arg Arg Arg
            20                  25                  30

Arg
```

<210> SEQ ID NO 15
<211> LENGTH: 96
<212> TYPE: DNA
<213> ORGANISM: Oncorhynchus mykiss
<220> FEATURE:
<221> NAME/KEY: CDS
<222> LOCATION: (1)..(93)
<220> FEATURE:
<221> NAME/KEY: misc_feature
<222> LOCATION: (21)..(21)
<223> OTHER INFORMATION: n = a or c or g or t
<220> FEATURE:
<221> NAME/KEY: misc_feature
<222> LOCATION: (30)..(30)
<223> OTHER INFORMATION: n = a or c or g or t
<220> FEATURE:
<223> OTHER INFORMATION: nucleotide sequence derived from amino acid
      sequence

<400> SEQUENCE: 15

```
atg ccc aga aga cgc aga gcn agc cga cgn gtc cgc agg cgc cgc cgc      48
Met Pro Arg Arg Arg Arg Ala Ser Arg Arg Val Arg Arg Arg Arg
 1               5                  10                  15 ccc agg gtg tcc cga cgt cgc agg aga gga ggc cgc agg agg cgt tag      96
Pro Arg Val Ser Arg Arg Arg Arg Arg Gly Gly Arg Arg Arg Arg
             20                  25                  30
```

<210> SEQ ID NO 16
<211> LENGTH: 31
<212> TYPE: PRT
<213> ORGANISM: Oncorhynchus mykiss
<220> FEATURE:
<223> OTHER INFORMATION: nucleotide sequence derived from amino acid
      sequence

<400> SEQUENCE: 16

```
Met Pro Arg Arg Arg Arg Ala Ser Arg Arg Val Arg Arg Arg Arg
 1               5                  10                  15

Pro Arg Val Ser Arg Arg Arg Arg Arg Gly Gly Arg Arg Arg Arg
             20                  25                  30
```

<210> SEQ ID NO 17
<211> LENGTH: 96
<212> TYPE: DNA
<213> ORGANISM: Oncorhynchus mykiss
<220> FEATURE:
<221> NAME/KEY: CDS
<222> LOCATION: (1)..(93)
<220> FEATURE:
<221> NAME/KEY: misc_feature
<222> LOCATION: 21
<223> OTHER INFORMATION: n = a or g or c or t
<220> FEATURE:
<221> NAME/KEY: misc_feature
<222> LOCATION: 30
<223> OTHER INFORMATION: n = a or g or c or t
<220> FEATURE:
<223> OTHER INFORMATION: nucleotide sequence derived from amino acid
      sequence

<400> SEQUENCE: 17

```
atg ccc aga aga cgc aga gcn agc cga cgn ath cgc agg cgc cgc cgc      48
Met Pro Arg Arg Arg Arg Ala Ser Arg Arg Ile Arg Arg Arg Arg
 1               5                  10                  15 ccc agg gtg tcc cga cgt cgc agg aga gga ggc cgc agg agg cgt tag      96
Pro Arg Val Ser Arg Arg Arg Arg Arg Gly Gly Arg Arg Arg Arg
             20                  25                  30
```

<210> SEQ ID NO 18

```
<211> LENGTH: 31
<212> TYPE: PRT
<213> ORGANISM: Oncorhynchus mykiss
<220> FEATURE:
<223> OTHER INFORMATION: nucleotide sequence derived from amino acid
      sequence

<400> SEQUENCE: 18

Met Pro Arg Arg Arg Arg Ala Ser Arg Arg Ile Arg Arg Arg Arg
 1               5                  10                  15

Pro Arg Val Ser Arg Arg Arg Arg Gly Gly Arg Arg Arg Arg
            20                  25                  30

<210> SEQ ID NO 19
<211> LENGTH: 102
<212> TYPE: DNA
<213> ORGANISM: Oncorhynchus mykiss
<220> FEATURE:
<221> NAME/KEY: CDS
<222> LOCATION: (1)..(99)
<220> FEATURE:
<223> OTHER INFORMATION: nucleotide sequence derived from amino acid
      sequence

<400> SEQUENCE: 19 atg ccc aga aga cgc aga aga tcc tcc agc cga cct ath cgc agg cgc      48
Met Pro Arg Arg Arg Arg Ser Ser Ser Arg Pro Ile Arg Arg Arg
 1               5                  10                  15 cgc cgc ccc agg gtg tcc cga cgt cgc agg aga gga ggc cgc agg agg      96
Arg Arg Pro Arg Val Ser Arg Arg Arg Arg Gly Gly Arg Arg Arg
            20                  25                  30 cgt tag                                                             102
Arg

<210> SEQ ID NO 20
<211> LENGTH: 33
<212> TYPE: PRT
<213> ORGANISM: Oncorhynchus mykiss
<220> FEATURE:
<223> OTHER INFORMATION: nucleotide sequence derived from amino acid
      sequence

<400> SEQUENCE: 20

Met Pro Arg Arg Arg Arg Arg Ser Ser Ser Arg Pro Ile Arg Arg Arg
 1               5                  10                  15

Arg Arg Pro Arg Val Ser Arg Arg Arg Arg Gly Gly Arg Arg Arg
            20                  25                  30

Arg

<210> SEQ ID NO 21
<211> LENGTH: 96
<212> TYPE: DNA
<213> ORGANISM: Clupea harengus
<220> FEATURE:
<221> NAME/KEY: CDS
<222> LOCATION: (1)..(93)
<220> FEATURE:
<221> NAME/KEY: misc_feature
<222> LOCATION: 27
<223> OTHER INFORMATION: n = a or g or c or t
<220> FEATURE:
<223> OTHER INFORMATION: nucleotide sequence derived from amino acid
      sequence

<400> SEQUENCE: 21 atg ccc aga aga cgc acc aga cgc gcn agc cga cct gtc cgc agg cgc      48
Met Pro Arg Arg Arg Thr Arg Arg Ala Ser Arg Pro Val Arg Arg Arg
```

```
                1               5                   10                  15
cgc ccc agg cgc gtg tcc cga cgt cgt cgc gca cgc cgc agg agg tag         96
Arg Pro Arg Arg Val Ser Arg Arg Arg Ala Arg Arg Arg
                20                  25                  30
```

<210> SEQ ID NO 22
<211> LENGTH: 31
<212> TYPE: PRT
<213> ORGANISM: Clupea harengus
<220> FEATURE:
<223> OTHER INFORMATION: nucleotide sequence derived from amino acid
      sequence

<400> SEQUENCE: 22

```
Met Pro Arg Arg Arg Thr Arg Arg Ala Ser Arg Pro Val Arg Arg
 1               5                   10                  15

Arg Pro Arg Arg Val Ser Arg Arg Arg Ala Arg Arg Arg
                20                  25                  30
```

<210> SEQ ID NO 23
<211> LENGTH: 99
<212> TYPE: DNA
<213> ORGANISM: Clupea harengus
<220> FEATURE:
<221> NAME/KEY: CDS
<222> LOCATION: (1)..(96)
<220> FEATURE:
<221> NAME/KEY: misc_feature
<222> LOCATION: 30
<223> OTHER INFORMATION: n = a or g or c or t
<220> FEATURE:
<223> OTHER INFORMATION: nucleotide sequence derived from amino acid
      sequence

<400> SEQUENCE: 23

```
atg gcc aga aga cgc aga agc aga cgc gcn agc cga cct gtc cgc agg       48
Met Ala Arg Arg Arg Ser Arg Arg Ala Ser Arg Pro Val Arg Arg
 1               5                   10                  15 cgc cgc ccc agg cgc gtg tcc cga cgt cgt cgc gca cgc cgc agg agg       96
Arg Arg Pro Arg Arg Val Ser Arg Arg Arg Ala Arg Arg Arg
                20                  25                  30 tag                                                                   99
```

<210> SEQ ID NO 24
<211> LENGTH: 32
<212> TYPE: PRT
<213> ORGANISM: Clupea harengus
<220> FEATURE:
<223> OTHER INFORMATION: nucleotide sequence derived from amino acid
      sequence

<400> SEQUENCE: 24

```
Met Ala Arg Arg Arg Ser Arg Arg Ala Ser Arg Pro Val Arg Arg
 1               5                   10                  15

Arg Arg Pro Arg Arg Val Ser Arg Arg Arg Ala Arg Arg Arg
                20                  25                  30
```

<210> SEQ ID NO 25
<211> LENGTH: 99
<212> TYPE: DNA
<213> ORGANISM: Clupea harengus
<220> FEATURE:
<221> NAME/KEY: CDS
<222> LOCATION: (1)..(96)
<220> FEATURE:
<223> OTHER INFORMATION: nucleotide sequence derived from amino acid
      sequence

<400> SEQUENCE: 25

| | | | | | | | | | | | | | | | | |
|---|---|---|---|---|---|---|---|---|---|---|---|---|---|---|---|---|
| atg | gcc | aga | aga | cgc | aga | tcc | tcc | agc | cga | cct | ath | cgc | agg | cgc | cgc | 48 |
| Met | Ala | Arg | Arg | Arg | Arg | Ser | Ser | Ser | Arg | Pro | Ile | Arg | Arg | Arg | | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ccc | agg | cgc | cgg | acc | aca | cgt | cgt | cgc | agg | gca | ggc | cgc | agg | agg | cgt | 96 |
| Pro | Arg | Arg | Arg | Thr | Thr | Arg | Arg | Arg | Arg | Ala | Gly | Arg | Arg | Arg | Arg | |
| | | | 20 | | | | | 25 | | | | | 30 | | | | tag                                                                 99

<210> SEQ ID NO 26
<211> LENGTH: 32
<212> TYPE: PRT
<213> ORGANISM: Clupea harengus
<220> FEATURE:
<223> OTHER INFORMATION: nucleotide sequence derived from amino acid
      sequence

<400> SEQUENCE: 26

Met Ala Arg Arg Arg Arg Ser Ser Ser Arg Pro Ile Arg Arg Arg
1               5                   10                  15

Pro Arg Arg Arg Thr Thr Arg Arg Arg Ala Gly Arg Arg Arg Arg
            20                  25                  30

<210> SEQ ID NO 27
<211> LENGTH: 111
<212> TYPE: DNA
<213> ORGANISM: Artificial Sequence
<220> FEATURE:
<221> NAME/KEY: misc_feature
<222> LOCATION: 30
<223> OTHER INFORMATION: n = a or g or c or t
<220> FEATURE:
<223> OTHER INFORMATION: Description of Artificial Sequence: consensus 1

<400> SEQUENCE: 27
atgsccagaa gacgcagaas cagaysckcn agmcsacstr thcgcaggcg ccgccgcscy        60
aggcgcskgw ccmsacgtcg tcgcaggaga gsasgccgca ggaggcgtta g                111

<210> SEQ ID NO 28
<211> LENGTH: 102
<212> TYPE: DNA
<213> ORGANISM: Artificial Sequence
<220> FEATURE:
<221> NAME/KEY: misc_feature
<222> LOCATION: 9
<223> OTHER INFORMATION: n = a or g or c or t
<220> FEATURE:
<221> NAME/KEY: misc_feature
<222> LOCATION: 12
<223> OTHER INFORMATION: n = a or g or c or t
<220> FEATURE:
<221> NAME/KEY: misc_feature
<222> LOCATION: 18
<223> OTHER INFORMATION: n = a or g or c or t
<220> FEATURE:
<221> NAME/KEY: misc_feature
<222> LOCATION: 42
<223> OTHER INFORMATION: n = a or g or c or t
<220> FEATURE:
<221> NAME/KEY: misc_feature
<222> LOCATION: 57
<223> OTHER INFORMATION: n = a or g or c or t
<220> FEATURE:
<221> NAME/KEY: misc_feature
<222> LOCATION: 78
<223> OTHER INFORMATION: n = a or g or c or t
<220> FEATURE:
<221> NAME/KEY: misc_feature
<222> LOCATION: 81
<223> OTHER INFORMATION: n = a or g or c or t
<220> FEATURE:
<221> NAME/KEY: misc_feature
<222> LOCATION: 93
<223> OTHER INFORMATION: n = a or g or c or t
<220> FEATURE:
<221> NAME/KEY: misc_feature
<222> LOCATION: 96
<223> OTHER INFORMATION: n = a or g or c or t
<220> FEATURE:
<223> OTHER INFORMATION: Description of Artificial Sequence: consensus 2

<400> SEQUENCE: 28
atgccccgnc gncgccgntc ctccagccga cctgtccgcc gncgccgccg ccccgngtg        60 tcccgacgtc gtcgccgncg nggaggccgc cgncgncgtt ag                         102

<210> SEQ ID NO 29
<211> LENGTH: 102
<212> TYPE: DNA
<213> ORGANISM: Artificial Sequence
<220> FEATURE:
<223> OTHER INFORMATION: Description of Artificial Sequence: consensus 3

<400> SEQUENCE: 29
atgccgcggc gccgccggtc gtcgagccgc ccggtgcgtc gccggcgccg cccgcgggtc       60
tcgcgccgcc gccggcgccg cggcggccgc cggcgccgct ga                         102

<210> SEQ ID NO 30
<211> LENGTH: 102
<212> TYPE: DNA
<213> ORGANISM: Artificial Sequence
<220> FEATURE:
<223> OTHER INFORMATION: Description of Artificial Sequence: consensus 4

<400> SEQUENCE: 30
atgccgcgcc gtcgccgtag ctcgagccgt ccggtgcgtc gccgtcgccg tccccgtgtc       60
agccgccgcc gccgtcgccg cggcggacgc cgtcgccgtt ga                         102

<210> SEQ ID NO 31
<211> LENGTH: 102
<212> TYPE: DNA
<213> ORGANISM: Artificial Sequence
<220> FEATURE:
<223> OTHER INFORMATION: Description of Artificial Sequence: consensus 5

<400> SEQUENCE: 31
atgccgcggc gtcggcgcag ctccagccgt ccagtgcggc gccgtcgccg ccccgtgtc        60 tcgcgccgcc gccggcgccg cggcggacgc cgtcgccggt ga                         102

<210> SEQ ID NO 32
<211> LENGTH: 102
<212> TYPE: DNA
<213> ORGANISM: Artificial Sequence
<220> FEATURE:
<223> OTHER INFORMATION: Description of Artificial Sequence: ebl 1

<400> SEQUENCE: 32
atgccgcggc gtcggcgtag ctccagccgt ccagtgcgtc gccgtcgccg ccccgtgtc        60 tcgcgccgcc gccggcgccg cggcggacgc cgtcgccgtt ga                         102

<210> SEQ ID NO 33
<211> LENGTH: 36
<212> TYPE: PRT

```
<213> ORGANISM: Artificial Sequence
<220> FEATURE:
<221> NAME/KEY: misc_feature
<222> LOCATION: 1
<223> OTHER INFORMATION: X= zero or M
<220> FEATURE:
<221> NAME/KEY: misc_feature
<222> LOCATION: 2
<223> OTHER INFORMATION: X= A or P
<220> FEATURE:
<221> NAME/KEY: misc_feature
<222> LOCATION: 6
<223> OTHER INFORMATION: X= zero or R
<220> FEATURE:
<221> NAME/KEY: misc_feature
<222> LOCATION: 7
<223> OTHER INFORMATION: X=zero or T or S
<220> FEATURE:
<221> NAME/KEY: misc_feature
<222> LOCATION: 8
<223> OTHER INFORMATION: X= zero or R
<220> FEATURE:
<221> NAME/KEY: misc_feature
<222> LOCATION: 9
<223> OTHER INFORMATION: X=zero or R or S
<220> FEATURE:
<221> NAME/KEY: misc_feature
<222> LOCATION: 10
<223> OTHER INFORMATION: X= S or A
<220> FEATURE:
<221> NAME/KEY: misc_feature
<222> LOCATION: 11
<223> OTHER INFORMATION: X= S or R
<220> FEATURE:
<221> NAME/KEY: misc_feature
<222> LOCATION: 12
<223> OTHER INFORMATION: X= R or P
<220> FEATURE:
<221> NAME/KEY: misc_feature
<222> LOCATION: 13
<223> OTHER INFORMATION: X= P or R
<220> FEATURE:
<221> NAME/KEY: misc_feature
<222> LOCATION: 14
<223> OTHER INFORMATION: X= V or I
<220> FEATURE:
<221> NAME/KEY: misc_feature
<222> LOCATION: 19
<223> OTHER INFORMATION: X= zero or R
<220> FEATURE:
<221> NAME/KEY: misc_feature
<222> LOCATION: 20
<223> OTHER INFORMATION: X= P or A
<220> FEATURE:
<221> NAME/KEY: misc_feature
<222> LOCATION: 22
<223> OTHER INFORMATION: X=   zero or R
<220> FEATURE:
<221> NAME/KEY: misc_feature
<222> LOCATION: 23
<223> OTHER INFORMATION: X= V or R
<220> FEATURE:
<221> NAME/KEY: misc_feature
<222> LOCATION: 24
<223> OTHER INFORMATION: X=   S or T
<220> FEATURE:
<221> NAME/KEY: misc_feature
<222> LOCATION: 25
<223> OTHER INFORMATION: X=   R or T
<220> FEATURE:
<221> NAME/KEY: misc_feature
<222> LOCATION: 29
<223> OTHER INFORMATION: X= zero or R
<220> FEATURE:
<221> NAME/KEY: misc_feature
<222> LOCATION: 30
<223> OTHER INFORMATION: X= zero or R
<220> FEATURE:
<221> NAME/KEY: misc_feature
```

```
<222> LOCATION: 31
<223> OTHER INFORMATION: X= G or A
<220> FEATURE:
<221> NAME/KEY: misc_feature
<222> LOCATION: 32
<223> OTHER INFORMATION: X= G or R
<220> FEATURE:
<221> NAME/KEY: misc_feature
<222> LOCATION: 36
<223> OTHER INFORMATION: X= zero or R
<220> FEATURE:
<223> OTHER INFORMATION: Description of Artificial Sequence: consensus
      sequence

<400> SEQUENCE: 33

Xaa Xaa Arg Arg Arg Xaa Xaa Xaa Xaa Xaa Xaa Xaa Xaa Xaa Arg Arg
 1               5                   10                  15

Arg Arg Xaa Xaa Arg Xaa Xaa Xaa Xaa Arg Arg Arg Xaa Xaa Xaa Xaa
            20                  25                  30

Arg Arg Arg Xaa
        35

<210> SEQ ID NO 34
<211> LENGTH: 227
<212> TYPE: DNA
<213> ORGANISM: Artificial Sequence
<220> FEATURE:
<221> NAME/KEY: CDS
<222> LOCATION: (43)..(108)
<220> FEATURE:
<221> NAME/KEY: CDS
<222> LOCATION: (109)..(207)
<220> FEATURE:
<223> OTHER INFORMATION: Description of Artificial Sequence: cloning
      sequence for expression of Protamine
<220> FEATURE:
<221> NAME/KEY: sig_peptide
<222> LOCATION: (43)..(108)
<223> OTHER INFORMATION: pelB gene
<220> FEATURE:
<221> NAME/KEY: misc_feature
<222> LOCATION: (1)..(6)
<223> OTHER INFORMATION: XbaI restriction site
<220> FEATURE:
<221> NAME/KEY: misc_feature
<222> LOCATION: (222)..(227)
<223> OTHER INFORMATION: Bam HI restriction site
<220> FEATURE:
<221> NAME/KEY: RBS
<222> LOCATION: (28)..(33)
<223> OTHER INFORMATION: IRES sequence
<220> FEATURE:
<221> NAME/KEY: gene
<222> LOCATION: (109)..(207)
<223> OTHER INFORMATION: ebl 1 gene

<400> SEQUENCE: 34
tctagaaata attttgttta actttaagaa ggagatatac at atg aaa tac ctg       54
                                              Met Lys Tyr Leu
                                               1 ctg ccg acc gct gct gct ggt ctg ctc ctc gct gcc cag ccg gcg          102
Leu Pro Thr Ala Ala Ala Gly Leu Leu Leu Leu Ala Ala Gln Pro Ala
 5                  10                  15                  20 atg gcc atg ccg cgg cgt cgg cgt agc tcc agc cgt cca gtg cgt cgc     150
Met Ala Met Pro Arg Arg Arg Ser Ser Ser Arg Pro Val Arg Arg
            25                  30                  35 cgt cgc cgc ccc cgt gtc tcg cgc cgc cgg cgc cgc ggc gga cgc         198
Arg Arg Arg Pro Arg Val Ser Arg Arg Arg Arg Arg Gly Gly Arg
        40                  45                  50 cgt cgc cgt tg    aggaatta attcggatcc                                227
Arg Arg Arg
```

-continued

```
Arg Arg Arg
        55

<210> SEQ ID NO 35
<211> LENGTH: 22
<212> TYPE: PRT
<213> ORGANISM: Artificial Sequence
<220> FEATURE:
<223> OTHER INFORMATION: Description of Artificial Sequence: cloning
      sequence for expression of Protamine

<400> SEQUENCE: 35

Met Lys Tyr Leu Leu Pro Thr Ala Ala Ala Gly Leu Leu Leu Leu Ala
  1               5                  10                  15

Ala Gln Pro Ala Met Ala
             20

<210> SEQ ID NO 36
<211> LENGTH: 33
<212> TYPE: PRT
<213> ORGANISM: Artificial Sequence
<220> FEATURE:
<223> OTHER INFORMATION: Description of Artificial Sequence: cloning
      sequence for expression of Protamine

<400> SEQUENCE: 36

Met Pro Arg Arg Arg Ser Ser Ser Arg Pro Val Arg Arg Arg
  1               5                  10                  15

Arg Pro Arg Val Ser Arg Arg Arg Arg Arg Gly Gly Arg Arg Arg
             20                  25                  30

Arg
```

METHOD FOR THE PRODUCTION OF PROTAMINE

FIELD OF THE INVENTION

This is a National Phase Application in the United States of International Patent Application No. PCT/EP02/06596 filed Jun. 14, 2002. The disclosure of the above patent application is hereby incorporated by reference.

The present invention generally relates to the fields of genetic engineering and biochemistry. In particular, it relates to a novel method for the production of protamine as well as to novel compositions containing protamine as active ingredient. Furthermore, it relates to the use of said compositions for killing or inhibiting microbial cells.

BACKGROUND OF THE INVENTION

The immoderate use of different antibiotics during the last six decades caused the emergence and the dissemination of bacterial populations expressing resistance to these substances. Interactions between microbial resistance and antibacterial agents occur either directly by the development of resistance to the agent used, to agents of the same class, or in an indirect way by the selection of resistant organisms when patients are treated with antibiotics, when the environment is contaminated with antibiotics (hospital) or when antibacterial agents are applied in agriculture and animal husbandry. Antimicrobial selection as well as contagion are the decisive processes responsible for the global spread and linking of resistance genes.

There is increased concern that because of the widespread use of antibiotics and the continuous increase of bacterial resistance, the pharmaceutical industry may no longer be able to develop effective novel antibiotics sufficiently rapidly (JACK et al. 1995). This fact quickens interest in microbially produced antibacterial peptides. In recent years, more than fifty antibacterial peptides produced by lactic acid bacteria have been isolated (NES and HOLO, 2000). These so-called bacteriocins contain 20-60 amino acids, are inhibitory in a nanomolar range and cause membrane permeabilization and leakage of sensitive cells. They are secreted by some bacterial strains, which are thus adapted to compete against other microorganisms in the same environmental compartment (NAVARRO et al. 2000).

Only a few microbially produced substances are known to be effective against gram-positive as well as gram-negative bacteria (BLACKBURN et al. 1989; STEVENS et al. 1991; KALCHAYANAND et al. 1992). One promising substance of biogenic origin possessing a broad antimicrobial spectrum (JOHANSEN et al. 1995; JOHANSEN et al. 1997; HANSEN and GILL 2000) is protamine, a basic peptide (pI>10) consisting of 32 amino acids, of which 21 are arginine (ANDO et al. 1973). Protamine is found enriched in sperm, e.g. in salmon spermatozoan nuclei, compacting DNA and taking the position of histones during the maturation of the spermatids (LOUIE and DIXON, 1974). Its effect on gram-negative bacteria is reported to be lower than on gram-positive bacteria (IsLAM et al. 1984; MULHOLLAND and MELLERSH 1987; YANAGIMOTO 1992; JOHANSEN et al. 1995).

There is an extremely high degree of sequence conservation in the coding and 3' untranslated regions of different rainbow trout protamine genes (AIKEN et al. 1983), showing cross-hybridization under less stringent conditions (SAKAI et al. 1981).

Protamine is also known for its antifungal activity (KAMAL et al. 1986).

The antimicrobial effect of protamine is supposed to be caused by its polycationic nature (HIRSCH 1958; JOHANSEN et al. 1995). A possible mode of action may consist in the binding of the peptide to the outer membrane, causing a malfunction and inducing channels into the membrane, as was proved for other cationic peptides (CHRISTENSEN et al. 1988; KAGAN et al. 1990).

It has been demonstrated that protamine causes a disruption of the cytoplasmatic membrane (JOHNSEN et al. 1997). It was furthermore shown that polycationic peptides like protamine can also activate autolysins, resulting in cell lysis, as well as inhibit phosphorylase activity (JOHANSEN et al. 1996). Protamine may also enter the cytoplasm, inhibiting genetic transformation (ANTHOI and POPESCU 1979). Protamine penetrates gram-negative bacteria and enhances the permeability of the outer membrane (VAARA and VAARA 1983; VAARA 1992). Furthermore, it deenergizes bacterial membranes and causes a reduction of cellular ATP content (ASPEDON and GROISMAN, 1996).

It has been shown that the antibacterial activity of protamine is dependent on the amount of bivalent cations stabilizing the outer membrane (JOHASEN et al. 1997) and the pH value (HANSEN and GILL 2000).

Protamine was shown to extend antibacterial effects against food-spoiling bacteria (JOHANSEN et al. 1996). Interestingly, STUMPE et al. (1998) found that OmpT, a protease from E. coli, is able to degrade protamine before it enters the bacterial cells. This fact has to be taken into consideration if protamine is used as a disinfectant or a replacement for antibiotics. It is of great importance that antibiotics are no longer to be permitted in the food industry after the end of 2003. Thus, new and effective substances have to be at disposal before that time.

WO 96/06532 discloses a protamine composition for killing or inhibiting microbial cells. The studies have been performed with protamine from Salmon (P-4005) obtained from Sigma Chemical Company (St. Louis, USA), dissolved in destined water, filter sterilized (0.2 μm) and used immediately after preparation. Besides protamine or protamine sulphate, the composition disclosed in WO 96/06532 additionally comprises a cell-wall degrading enzyme and/or an oxidoreductase and allegedly displays bactericidal, bacteriostatic, fungicidal and/or fungistatic properties. Accordingly and due to its broad range of activity against target organisms, protamine containing preparations have already been suggested for detergent and hard surface cleaning compositions and in methods for killing microbial cells present on a hard surface, for killing microbial cells or inhibiting growing microbial cells present on laundry, for killing microbial cells present on human or animal skin, mucous membranes, wounds, bruises or in the eye, as well as for the preservation of food, beverages, cosmetics, contact lens products, food ingredients or enzyme compositions.

Furthermore, protamine and suitable derivatives thereof display important physiological functions and have been suggested for medical use. For example, protamine has proven as a clinical heparin antagonist, e.g. to reduce post-operative bleeding, and is routinely administered after cardiac and vascular surgery to reverse the anticoagulant activity of heparin. In addition, protamine prolongs the adsorption of insulin, and is therefore combined with insulin to formulate protamine zinc insulin (PZI) and neutral protamine Hagedorn (NPH) insulin. Such formulations allow insulin-dependent diabetic patients to achieve euglycemia with less frequent insulin injections.

However, despite its universal use in clinical practice, current formulations of protamine are nevertheless toxic. Protamine toxicity ranges from mild hypotension to severe systemic vascular collapse requiring prompt intervention, or idiosyncratic fatal cardiac arrest. This drawback has been addressed in WO 00/55196 relating to low molecular weight (LMW) bioactive protamines and compositions, allegedly having reduced immunogenicity, antigenicity and/or toxicity compared to native protamine. According to the teaching of WO 00/55196, native salmine® (salmon) or clupeine® (herring) protamine commercially available from Sigma Chem. Co. is contacted with a proteolytic composition to generate LMW protamine fragments which can subsequently be used to select appropriate fragments, polypeptides, species of fractions of interest. However, WO 00/55196. does not provide any sequence information for the LMW protamine fragments.

It has thus been shown, that there is an increasing demand for protamine and/or its derivatives. Although it is stated in the art, that protamine can be isolated from mammals, amphibians and fish, and although is has long been speculated in the art to provide protamine as a recombinant protein, no evidence of recombinant production has yet been published with the effect, that salmon (salmine®) and herring (clupeine®) protamine remain to be the only commercially available preparations to date.

Thus, the main object underlying the present invention is to overcome the drawbacks of the state of the art by providing a method for recombinantly producing bioactive protamine or functional fragments thereof enabling large-scale, cost-effective and reliable production of this interesting substance.

SUMMARY OF THE INVENTION

The present invention provides means and methods of transforming bacteria, yeast, fungi, insect, animal and plant cells, seeds, tissues and whole organisms in order to yield transformants capable of expressing a bioactive protamine polypeptide or functional fragment thereof (protamine). The present invention further provides means and methods to recombinantly produce protamine using cells, tissues, organs or whole organisms which, after appropriate transformation, accumulate protamine. The present invention also provides DNA molecules encoding protamine derived from different sources and taxonomic groups of living organisms designed to be suitable for carrying out the method of the invention, and plasmids or vector systems comprising said molecules. Furthermore, the present invention provides transgenic bacteria, yeast, fungi, insect, animal and plant cells, seeds, tissues and whole organisms that are capable of producing protamine and contain the above DNA molecule(s) and/or that have been generated by use of the methods of the present invention. Additionally, the present invention provides antibodies displaying a specific immunoreactivity with a protamine polypeptide which are suitable for diagnostic and screening purposes as well as for isolating and purifying said polypeptide. Furthermore, the present invention provides a biological composition with bacteriocidal, bacteriostatic, fungicidal and/or fungistatic activity.

Additionally, the present invention provides pharmaceutical preparations comprising a protamine polypeptide or functional active fragments thereof as active ingredient.

Finally, the present invention provides means and methods for use of the protamine and compositions according to the invention.

DETAILED DESCRIPTION OF THE INVENTION

In the present context, the term "bacteriocidal" is to be understood as capable of killing bacterial cells.

In the present context, the term "bacteriostatic" is to be understood as capable of inhibiting bacterial growth, i.e. inhibiting growing bacterial cells. In the present context, the term "fungicidal" is to be understood as capable of killing fungal cells.

In the present context, the term "fungistatic" is to be understood as capable of inhibiting fungal growth, i.e. inhibiting growing fungal cells.

The term "growing cell" is to be understood as a cell having access to a suitable nutrient and thus being capable of reproduction/propagation. By the term "non-growing cell" is meant a living, but dormant, cell, i.e. a cell in the non-growing, non-dividing, non-multiplying and non-energized state with metabolic processes at a minimum.

The term "microbial cells" denotes bacterial or fungal cells.

The terms "native", "of biological origin" and "from native or biological sources" are to be understood that a protamine polypeptide or functional fragment thereof is isolated, recovered or regenerated or that corresponding amino and nucleic acid sequence information is obtained or derived from biological material such as humans, animals or plants. These terms additionally include protamine polypeptides or functional fragments thereof which have been recombinantly produced according to the method of the invention on the basis of coding sequences obtained or derived from native or biological sources. Similarly, the term "of microbiological origin" denotes that the substance or compounds are recovered or regenerated from microbiological material such as bacteria, fungi, yeast or that a parent or native substance or compound is producible by a microbiological organism.

The terms "synthesized polypeptide" and "multimeric forms" refer to a synthesized assembly, i.e. a chain, built of peptide monomers. The protamine polypeptides and functional fragments thereof contemplated by the present invention are basic polypeptides, i.e. polylysins and polyarginins, and co-polymers thereof. It is preferred that the polypeptides have a chain length of less than about 100 amino acids but is contemplated that polypeptides of less than ?? kD are useful. Preferably, the polypeptides to be produced or used or which are active ingredients in a composition or pharmaceutical preparation according to the invention are of almost identical chain length or molecular weight but mixtures of polypeptides having various chain lengths or molecular weights are also useful.

Preferred basic proteins to be used in the compositions of the present invention are protamines, protamine sulphates, defensins, magainins, mellitin, cecropins and protegrins, with protamines and protamine sulphates being preferred. The terms "protamine(s)", "protamine protein(s)" and "protamine (poly)peptide(s)" as used herein are meant to comprise any protamine amino acid sequence obtained or derived from native or biological sources including fragments thereof and multimeric forms of said amino acid sequence or fragment thereof. Furthermore, these terms encompass (synthesized) polypeptides which are artificial and specifically designed for specific purposes and cannot be isolated from native or biological sources.

The term "biologically active" protamine denotes any protamine amino acid sequence displaying at least one biological activity of protamine as already known in the art. Included are also protamines which as such are not biologically active but which can be converted into biologically active forms, e.g. by treating said protamines with substances such as chaperone proteins commercially available.

The term "functional fragment" of protamine denotes any protamine amino acid sequence or peptide retaining at least one of the biological activities as discussed in the art or as mentioned above. Furthermore, said term comprises protamine amino acid sequences which retain at least one common structural or antigenic determinant as mentioned hereinbelow. In particular, functional fragments comprise those disclosed herein as well as those which can easily be produced on the basis of information provided herein.

Although the method of recombinantly producing bioactive protamine has only been exemplified hereinbelow with respect to the use of DNA sequence information gathered from fish, the present invention also provides DNA probes and sequence information which allow the person skilled in the art to clone the corresponding genes and/or cDNAs from other sources such as birds and mammals.

According to a preferred embodiment, these DNA sequences are in the form of cDNAs, genomic or manufactured (synthetic) DNA sequences and can be prepared as known in the art (see e.g. Sambrook et al., s.a.) or e.g. as specifically described hereinbelow.

Given the guidance provided herein, the nucleic acids of the invention are obtainable according to methods well known in the art. For example, a DNA of the invention is obtainable by chemical synthesis, using polymerase chain reaction (PCR) or by screening a genomic library or a suitable cDNA library prepared from a source believed to possess protamine and to express it at a detectable level.

Nucleic acid molecules and vectors according to the present invention may be provided in a form isolated and/or purified from their natural environment, in substantially pure or homogeneous, or free or substantially free of nucleic acid and or genes of the species of interest or origin other than the relevant sequence. Nucleic acid according to the-present invention may include cDNA, RNA, genomic DNA and may be wholly or partially synthetic. The term "isolate" where used may encompass any of these possibilities.

Nucleic acid as herein provided or obtainable by use of the disclosures herein, may be the subject of alteration by way of one or more of addition, insertion, deletion or substitution of nucleotides with or without altering the encoded amino acid sequence (by virtue of the degeneracy of the genetic code). Such altered forms of protamine nucleotide sequences as herein provided or obtainable by use of the disclosures herein can be easily and routinely tested for both protamine function and protamine function in accordance with standard techniques e.g. as provided herein.

Chemical methods for synthesis of a nucleic acid of interest are known in the art and include triester, phosphite, phosphoramidite and H-phosphonate methods, PCR and other autoprimer methods as well as oligonucleotide synthesis on solid supports. These methods may be used if the entire nucleic acid sequence of the nucleic acid is known, or the sequence of the nucleic acid complementary to the coding strand is available. Alternatively, if the target amino acid sequence is known, one may infer potential nucleic acid sequences using known and preferred coding residues for each amino acid residue.

An alternative means to isolate the gene encoding protamine is to use PCR technology as described e.g. in section 14 of Sambrook et al., 1989. This method requires the use of oligonucleotide probes that will hybridise to protamine nucleic acid. Strategies for selection of oligonucleotides are described below.

Libraries are screened with probes or analytical tools designed to identify the gene of interest or the protein encoded by it. For cDNA expression libraries suitable means include monoclonal or polyclonal antibodies that recognise and specifically bind to protamine; oligonucleotides of about 20 to 80 bases in length that encode known or suspected protamine cDNA from the same or different species; and/or complementary or homologous cDNAs or fragments thereof that encode the same or a hybridising gene. Appropriate probes for screening genomic DNA libraries include, but are not limited to oligonucleotides, cDNAs or fragments thereof that encode the same or hybridising DNA; and/or homologous genomic DNAs or fragments thereof.

A nucleic acid encoding protamine may be isolated by screening suitable cDNA or genomic libraries under suitable hybridisation conditions with a probe, i.e. a nucleic acid disclosed herein including oligonucleotides derivable from any of the sequences as set forth in SEQ ID NOS. 1, 3, 5, 7, 9, 11, 13, 15, 17, 19, 21, 23, 25, 27, 28, 29, 30, 31, 32, and 34. Suitable libraries are commercially available or can be prepared e.g. from cell lines, tissue samples, and the like.

As used herein, a probe is e.g. a single-stranded DNA or RNA that has a sequence of nucleotides that includes between 10 and 50, preferably between 15 and 30 and most preferably at least about 20 contiguous bases that are the same as (or the complement of) an equivalent or greater number of contiguous bases, e.g. as set forth in any of the SEQ ID's- mentioned above. The nucleic acid sequences selected as probes should be of sufficient length and sufficiently unambiguous so that false positive results are minimised. The nucleotide sequences are usually based on conserved or highly homologous nucleotide sequences or regions of protamine as already mentioned hereinbefore. The nucleic acids used as probes may be degenerate at one or more positions. The use of degenerate oligonucleotides may be of particular importance where a library is screened from a species in which preferential codon usage in that species is not known.

Preferred regions from which to construct probes include 5' and/or 3' coding sequences, sequences predicted to encode ligand binding sites, and the like. For example, either the full-length cDNA clone disclosed herein or fragments thereof can be used as probes. Preferably, nucleic acid probes of the invention are labelled with suitable label means for ready detection upon hybridisation. For example, a suitable label means is a radiolabel. The preferred method of labelling a DNA fragment is by incorporating $\alpha^{32P}$ dATP with the Klenow fragment of DNA polymerase in a random priming reaction, as is well known in the art. Oligonucleotides are usually end-labelled with $\gamma^{32P}$-labelled ATP and polynucleotide kinase. However, other methods (e.g. non-radioactive) may also be used to label the fragment or oligonucleotide, including e.g. enzyme labelling, fluorescent labelling with suitable fluorophores and biotinylation.

After screening the library, e.g. with a portion of DNA including substantially the entire protamine-encoding sequence or a suitable oligonucleotide based on a portion of said or equivalent DNA, positive clones are identified by detecting a hybridisation signal; the identified clones are characterised by restriction enzyme mapping and/or DNA sequence analysis, and then examined, e.g. by comparison with the sequences set forth herein, to ascertain whether they include DNA encoding a complete protamine (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNAs and deduced amino acid sequences provided herein.

In order to detect any abnormality of endogenous protamine, genetic screening may be carried out using the nucleotide sequences of the invention as hybridisation probes.

It is envisaged that the nucleic acids of the invention can be readily modified by nucleotide substitution, nucleotide deletion, nucleotide insertion or inversion of a nucleotide stretch, and any combination thereof. Such mutants can be used e.g. to produce a protamine mutant that has an amino acid sequence differing from the protamine sequences as found in nature. Mutagenesis may be predetermined (site-specific) or random. A mutation which is not a silent mutation must not place sequences out of reading frames and preferably will not create complementary regions that could hybridise to produce secondary mRNA structure such as loops or hairpins.

Furthermore, the present invention envisages and enables the use of the sequence data provided herein to conduct relational and functional genomic studies. Relational studies are used as adjuncts to sequencing and mapping activities, and are designed to provide interesting, and potentially important, hints about biological function including e.g. homology searches, secondary structure correlations, differential cDNA screening, expression cloning, genetic linkage analysis, positional cloning and mutational analysis. In contrast to relational studies, functional studies generally make use of cells or animals to attempt a more direct correlation of sequence and biological function and include e.g. screening for phenotypic changes in systems such as yeast, flies, mitochondria, human tissues, mice, and frogs, using gene "knockouts" or other methods intended to control gene expression or protein action in order to provide information useful in relating sequences to function. These techniques as such are well-known in the art.

Use of the above approaches should preferably achieve one or more of the following criteria: (a) inhibition of the gene sequence should be sequence-specific in order to substantially eliminate false-positive results; (b) should have a broad based applicability, i.e. it should be possible to work with both high and low abundance genes, as well as with sequences whose product may be intracellular, membrane-associated, or extracellular; (c) should be applicable in models predictive of the (human) condition of interest; (d) should allow dose-response studies to be conducted e.g. in order to determine the dose at which the target is most affected; (e) the amount of information needed for target validation studies preferably should be minimal, i.e. the technique e.g. allows for dealing directly with ESTs without the former requirement of obtaining full-length gene sequences, promoter and other regulatory information, or protein sequence/structure; (f) should be useable in a high-throughput mode.

Accordingly, the present invention provides sufficient guidance to apply all approaches and techniques described above including "knockouts", intracellular antibodies, aptamers, antisense oligonucleotides, and ribozymes. In a preferred embodiment of the present invention, protamine-specific antisense oligonucleotides derived from any of the sequences as set forth in SEQ ID NOS. 1, 3, 5, 7, 9, 11, 13, 15, 17, 19, 21, 23, 25, 27, 28, 29, 30, 31, 32, and 34 can be used in order to identify the minimum sequence information needed to generate bioactive protamine. In a further preferred embodiment, use is made of specifically designed ribozymes which deliver optimized sequence-specific inhibition by manipulating elements inherent to their mechanism of action. For example, ribozymes can be designed to bind only to their targets, and by chosing a target sequence of 15 nucleotides—well within the informational limits of typical ESRs—there is assurance, on a statistical basis, that the target sequence will appear only once in the genome. Accordingly, the invention generally provides ribozymes specifically designed to interact only with its target which is expected to appear only once in the genome, ensuring a high degree of assurance that only the specific target has been inhibited. More particularly, the invention provides ribozymes which are uniquely equipped to deliver several types of important controls that can verify that inhibition of a specific mRNA target was the actual cause of alteration of protamine-mediated conditions or phenotypes. It is known, for example, that mutating the ribozyme's catalytic core renders it incapable of cleavage but still functional in terms of highly specific binding to its target. These "inactivated" ribozymes produce either no or substantially reduced target inhibition relative to the active ribozyme—making them a very effective negative control. Alternatively, the catalytic core can be maintained in its active form, but the target arms are modified such that they will not bind the target sequence. If nonspecific cleavage is occurring, such a construct should show activity. Since ribozymes contain noncontiguous binding arms, each of the ribozyme's two binding arms binds seperately and adds to ribozyme selectivity while maintaining specificity. Due to the low binding strength of such noncontiguous binding arms compared to e.g. contiguous antisense binding, any mismatches between the ribozyme and the target sequence will not be expected to bind effectively and thus allow the target to fall off before cleavage.

For the approaches and techniques as exemplified above, both the entire sequence as set forth in any of SEQ ID NOS. 1, 3, 5, 7, 9, 11, 13, 15, 17, 19, 21, 23, 25, 27, 28, 29, 30, 31, 32, and 34, as well as fragments thereof, in particular those described herein or those which encode an amino acid sequence selected from the group consisting of amino acid sequences extending from position 9 to position 18, from position 9 to position 20, from position 9 to position 21, from position 9 to position 22, from position 9 to position 23, from position 10 to position 20, from position 10 to position 21, from position 10 to position 22, from position 10 to position 23, and from position 10 to 24 of SEQ ID NO. 2, can be used.

If required, nucleic acids encoding protamine-related proteins or polypeptides can be cloned from cells or tissues according to established procedures using probes derived from protamine. In particular, such DNAs can be prepared by:

a) isolating mRNA from suitable cells or tisues, selecting the desired mRNA, for example by hybridisation with a DNA probe or by expression in a suitable expression system, and screening for expression of the desired polypeptide, preparing single-stranded cDNA complementary to that mRNA, then double-stranded cDNA therefrom, or b) isolating cDNA from a cDNA library and selecting the desired cDNA, for example using a DNA probe or using a suitable expression system and screening for expression of the desired polypeptide, or c) incorporating the double-stranded DNA of step a) or b) into an appropriate expression vector, d) transforming appropriate host cells with the vector and isolating the desired DNA.

Polyadenylated messenger RNA (step a) is isolated by known methods. Isolation methods involve, for example, homogenizing cells in the presence of a detergent and a ribonuclease inhibitor, for example heparin, guanidinium isothiocyanate or mercaptoethanol, extracting the mRNA with a chloroform-phenol mixture, optionally in the presence of salt and buffer solutions, detergents and/or cation chelating agents, and precipitating mRNA from the remaining aqueous, salt-containing phase with ethanol, isopropanol or the like. The isolated mRNA may be further purified by centrifuging in a caesium chloride gradient followed by ethanol precipitation and/or by chromatographic methods, for example affinity chromatography, for example chromatography on oligo (dT) cellulose or on oligo (U) sepharose. Preferably, such purified total mRNA is fractionated according to size by gradient centrifugation, for example in a linear sucrose gradient, or chromatography on suitable size fractionation columns, for example on agarose gels.

The desired mRNA is selected by screening the mRNA directly with a DNA probe, or by translation in suitable cells or cell-free systems and screening the obtained polypeptides. The selection of the desired mRNA is preferably achieved using a DNA hybridisation probe, thereby avoiding the additional step of translation. Suitable DNA probes are DNAs of known nucleotide sequence consisting of at least 17 nucleotides derived from DNAs encoding protamine or a related protein. Alternatively, EST sequence information can be used to generate suitable DNA probes.

Synthetic DNA probes are synthesised according to known methods as detailed hereinbelow, preferably by stepwise condensation using the solid phase phosphotriester, phosphite triester or phosphoramidite method, for example the condensation of dinucleotide coupling units by the phosphotriester method. These methods are adapted to the synthesis of mixtures of the desired oligonucleotides by using mixtures of two, three or four nucleotides dA, dC, dG and/or dT in protected form or the corresponding di-nucleotide coupling units in the appropriate condensation step as described by Y. Ike et al. (Nucleic Acids Research 11, 477, 1983).

For hybridisation, the DNA probes are labelled, for example radioactively labelled by the well known kinase reaction. The hybridisation of the size-fractionated mRNA with the DNA probes containing a label is performed according to known procedures, i.e. in buffer and salt solutions containing adjuncts, for example calcium chelators, viscosity regulating compounds, proteins, irrelevant DNA and the like, at temperatures favouring selective hybridisation, for example between 0° C. and 80° C., for example between 25° C. and 50° C. or around 65° C., preferably at around 20° lower than the hybrid double-stranded DNA melting temperature.

Fractionated mRNA may be translated in cells, for example frog oocytes, or in cell-free systems, for example in reticulocyte lysates or wheat germ extracts. The obtained polypeptides are screened for protamine activity or for reaction with antibodies raised against protamine or the protamine-related protein, for example in an immunoassay, for example radioimmunoassay, enzyme immunoassay or immunoassay with fluorescent markers. Such immunoassays and the preparation of polyclonal and monoclonal antibodies are well known in the art and are applied accordingly. According to the invention there are provided polyclonal antibodies.

The preparation of a single-stranded complementary DNA (cDNA) from the selected mRNA template 'is well known in the art, as is the preparation of a double-stranded DNA from a single-stranded DNA. The mRNA template is incubated with a mixture of deoxynucleoside triphosphates, optionally radioactively labelled deoxynucleoside triphosphates (in order to be able to screen the result of the reaction), a primer sequence such as an oligo-dT residue hybridising with the poly(A) tail of the mRNA and a suitable enzyme such as a reverse transcriptase for example from avian myeloblastosis virus (AMV). After degradation of the template mRNA for example by alkaline hydrolysis, the cDNA is incubated with a mixture of deoxynucleoside triphosphates and a suitable enzyme to give a double-stranded DNA. Suitable enzymes are for instance a reverse transcriptase, the Klenow fragment of E. coli DNA polymerase I or T4 DNA polymerase. Usually, a hairpin loop structure formed spontaneously by the single-stranded cDNA acts as a primer for the synthesis of the second strand. This hairpin structure is removed by digestion with S1 nuclease. Alternatively, the 3'-end of the single-stranded DNA is first extended by homopolymeric deoxynucleotide tails prior to the hydrolysis of the mRNA template and the subsequent synthesis of the second cDNA strand.

In the alternative, double-stranded cDNA is isolated from a cDNA library and screened for the desired cDNA (step b). The cDNA library is constructed by isolating mRNA from suitable cells, and preparing single-stranded and double-stranded cDNA therefrom as described above. This cDNA is digested with suitable restriction endonucleases and incorporated into λ phage, for example λ charon 4A or λ gt11 following established procedures. The cDNA library replicated on nitrocellulose membranes is screened by using a DNA probe as described hereinbefore, or expressed in a suitable expression system and the obtained polypeptides screened for reaction with an antibody specific for the desired protamine.

A variety of methods are known in the art for the incorporation of double-stranded cDNA into an appropriate vector (step c). For example, complementary homopolymer tracts may be added to the double-stranded DNA and the vector DNA by incubation in the presence of the corresponding deoxynucleoside triphosphates and an enzyme such as terminal deoxynucleotidyl transferase. The Vector and double-stranded DNA are then joined by base pairing between the complementary homopolymeric tails and finally ligated by specific joining enzymes such as ligases. Other possibilities are the addition of synthetic linkers to the termini of the double-stranded DNA, or the incorporation of the double-stranded DNA into the vector by blunt- or-staggered-end ligation.

The transformation of appropriate host cells with the obtained hybrid vector (step d) and the selection of transformed host cells (step e) are well known in the art. Hybrid vectors and host cells may be particularly suitable for the production of DNA, or for the production of the desired protamine.

In addition to being useful for the production of recombinant protamine protein, these nucleic acids are also useful as probes, thus readily enabling those skilled in the art to identify and/or isolate nucleic acid encoding protamine. The nucleic acid may be unlabelled or labelled with a detectable moiety. Furthermore, the nucleic acids according to the invention are useful e.g. in a method determining the presence or even quantity of protamine specific nucleic acid, said method comprising hybridising the DNA (or RNA) encoding (or complementary to) protamine to test sample nucleic acid and determining the presence and, optionally, the amount of protamine. In another aspect, the invention provides a nucleic acid sequence that is complementary to, or hybridises under stringent conditions to, a nucleic acid sequence encoding protamine. These oligonucleotides can efficiently be used in antisense and/or ribozyme approaches, including gene therapy.

The invention also provides a method for amplifying a nucleic acid test sample comprising priming a nucleic acid polymerase (chain) reaction with nucleic acid (DNA or RNA) encoding (or complementary to) protamine.

The DNA-sequences of the present invention can thus be used as a guideline to define new PCR primers for the cloning of substantially homologous DNA sequences from other sources. In addition they and such homologous DNA sequences can be integrated into vectors by methods known in the art and described by e.g. Sambrook et al. (s.a.) to express or overexpress the encoded polypeptide(s) in appropriate host systems. However, a person skilled in the art knows that also the DNA-sequences themselves can be used to transform the suitable host systems of the invention to get overexpression of the encoded polypeptide or functional fragment thereof.

The nucleic acid molecule may be in the form of a recombinant and preferably replicable vector for example a plasmid, cosmid, phage or binary vector, e.g. suitable for use with bacteria such as those belonging to the genus of *Rhodopseudomonas, Pseudomonas* and *Escherichia*. The nucleic acid may be under the control of an appropriate promoter and regulatory elements for expression in a host cell such as a microbial, e.g. bacterial, animal (mammalian), yeast or plant cell. In the case of genomic DNA, this may contain its own promoter and regulatory elements and in the case of cDNA this may be under the control of an appropriate promoter and regulatory elements for expression in the host cell. Thus, the nucleotide sequence of SEQ ID NO. 32 (for example) may be placed under the control of a heterologous promoter. Similarly, a protamine homologue sequence from another species may be operably linked to a promoter other than that with which it is naturally associated. However, a vector including nucleic acid according to the present invention need not include a promoter, particularly if the vector is to be used to introduce the nucleic acid into cells for recombination into the genome or when used for promoter-trapping.

Those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992. The disclosures of Sambrook et al. and Ausubel et al. are incorporated herein by reference. Specific procedures and vectors previously used with wide success upon plants are described by Bevan (Nucl. Acids Res. 12, 8711-8721 (1984)) and Guerineau and Mullineaux (1993) (Plant transformation and expression vectors. In: Plant Molecular Biology Labfax (Croy RRD ed) Oxford, BIOS Scientific Publishers, pp 121-148).

As outlined above, the present invention thus provides specific DNA molecules as well as plasmid or vector systems comprising the same which comprise a DNA sequence within an operable expression cassette capable of directing production of a functionally active protamine. Preferably, said DNA molecules further comprise at least one selectable marker gene or cDNA operably linked to a constitutive, inducible or tissue-specific promoter sequence allowing its expression in bacteria, yeast, fungi, insect, animal or plant cells, seeds, tissues or whole organisms. If plastid-containing material is selected for transformation it is preferred that the coding nucleotide sequence is fused with a suitable plastid transit peptide encoding sequence, both of which preferably are expressed under the control of a tissue-specific or constitutive promoter.

The nucleic acid as provided by the present invention may be placed under the control of an inducible gene promoter thus placing expression under the control of the user.

In a further aspect the present invention provides a gene construct including an inducible promoter operatively linked to a nucleotide sequence provided by the present invention.

As discussed, this enables control of expression of the gene. The invention also provides suitable hosts or host cells transformed with said gene construct and methods including introduction of such a construct into a suitable host or host cell and/or induction of expression of a construct within a suitable host or host cell, e.g by application of a suitable stimulus, such as an effective exogenous inducer.

The term "inducible" as applied to a promoter is well understood by those skilled in the art. In essence, expression under the control of an inducible promoter is "switched on" or increased in response to an applied stimulus (which may be generated within a cell or provided exogenously). The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level which brings about the desired phenotype. One example of an inducible promoter is the ethanol inducible gene switch disclosed in Caddick et al (1998) Nature Biotechnology 16: 177-180. Many other examples will be known to those skilled in the art. An example of a suitable plant promoter may be the Cauliflower Mosaic Virus 35S (CaMV 35S) gene promoter that is expressed at a high level in virtually all plant tissues (Benfey et al, (1990) EMBO J 9: 1677-1684).

Polypeptides according to the invention include protamine and derivatives thereof which retain at least one common structural determinant of protamine.

"Common structural determinant" means that the derivative in question possesses at least one structural feature of protamine. Structural features includes possession of an epitope or antigenic site that is capable of cross-reacting with antibodies raised against a naturally occurring or denatured protamine polypeptide or fragment thereof, possession of amino acid sequence identity with protamine and features having common a structure/function relationship. Thus, protamine as provided by the present invention includes splice variants encoded by mRNA generated by alternative splicing of a primary transcript, amino acid mutants, glycosylation variants and other covalent derivatives of protamine which retain the physiological and/or physical properties of protamine. Exemplary derivatives include molecules wherein the protein of the invention is covalently modified by substitution, chemical, enzymatic, or other appropriate means with a moiety other than a naturally occurring amino acid. Such a moiety may be a detectable moiety such as an enzyme or a radioisotope. Further included are naturally occurring variants or homologues of protamine found with a particular species. Such a variant or homologue may be encoded by a related gene of the same gene family, by an allelic variant of a particular gene, or represent an alternative splicing variant of the protamine gene.

The protamine homologue may at the nucleotide level have homology with a nucleotide sequence as set forth in any of SEQ ID NOS. 1, 3, 5, 7, 9, 11, 13, 15, 17, 19, 21, 23, 25, 27, 28, 29, 30, 31, 32, and 34, or may encode a polypeptide which has homology with the protamine polypeptides or functional fragments according to the invention as set forth in any of SEQ ID NOS. 2, 4, 6, 8, 10, 12, 14, 16, 18, 20, 22, 24, and 34, preferably at least about 50%, 51%, 52%, 53%, 54% or 55%, or at least about 60%, or at least about 65%, or at least about 70%, or at least about 75%, or at least about 80% homology, or at least about 90% homology. Most preferably, at least about 95% or greater homology. (Determination of homology at the amino acid level is discussed further below.)

In certain embodiments, a polypeptide allele, variant, derivative, mutant derivative, mutant or homologue of the specific sequences may show little overall homology, say about 20%, or about 25%, or about 30%, or about 35%, or about 40% or about 45%, with the protamine amino acid sequences such as those set forth in any of SEQ ID NOS. 2, 4, 6, 8, 10, 12, 14, 16, 18, 20, 22, 24, 26, and 33, including fragments extending from position 9 to position 18, from position 9 to position 20, from position 9 to position 21, from position 9 to position 22, from position 9 to position 23, from position 10 to position 20, from position 10 to position 2 1, from position 10 to position 22, from position 10 to position 23, and from position 10 to 24 of SEQ ID NO. 2. Preferably, any such polypeptide alleles, variants, derivatives, mutant derivatives, mutants or homologues have 95%, 96%, 97%, 98%, 99%, or 100% identity with any of the sequences mntioned above. However, in any functionally significant domains or regions the amino acid percentage identity may be much higher, for example, as discussed above for the functional fragments disclosed herein. Putative functionally significant domains or regions can be identified using processes of bioinformatics, including comparison of the sequences of homologues.

Functionally significant domains or regions of different polypeptides may be combined for expression from encoding nucleic acid as a fusion protein. For example, particularly advantageous or desirable properties of different homologues may be combined in a hybrid protein, such that the resultant expression product, with protamine function, may include fragments of various parent proteins.

Similarity of amino acid sequences may be as defined and determined by the TBLASTN program, of Altschul et al. (1990) *J. Mol. Biol.* 215: 403-10, which is in standard use in the art. In particular, TBLASTN 2.0 may be used with Matrix BLOSUM62 and GAP penalties: existence: 11, extension: 1. Another standard program that may be used is BestFit, which is part of the Wisconsin Package, Version 8, September 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman (Adv. Appl. Math. (1981) 2: 482-489). Other algorithms include GAP, which uses the Needleman and Wunsch algorithm to align two complete sequences that maximizes the number of matches and minimizes the number of gaps. As with any algorithm, generally the default parameters are used, which for GAP are a gap creation penalty=12 and gap extension penalty=4. Alternatively, a gap creation penalty of 3 and gap extension penalty of 0.1 may be used. The algorithm FASTA (which uses the method of Pearson and Lipman (1988) *PNAS USA* 85: 2444-2448) is a further alternative.

Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions. Further discussion of polypeptides according to the present invention, which may be encoded by nucleic acid according to the present invention, is found herein.

Protamine fragments that are functional in the context of the present invention are also included within the ambit of the invention. Examples for such functional fragments include amino acid sequences extending from position 9 to position 18, from position 9 to position 20, from position 9 to position 21, from position 9 to position 22, from position 9 to position 23, from position 10 to position 20, from position 10 to position 21, from position 10 to position 22, from position 10 to position 23, and from position 10 to 24 of SEQ ID NO. 2.

The obtaining of homologues is later discussed herein, but briefly here it should be pointed out that the nucleotide sequence information provided herein, or any part thereof, may be used in a data-base search to find homologous sequences, expression products of which can be tested for protamine function.

By sequencing homologues, studying their expression patterns and examining the effect of altering their expression, genes carrying out a similar function to protamine are obtainable. Of course, mutants, variants and alleles of these sequences are included within the scope of the present invention in the same terms as discussed above for the protamine genes discussed herein, although it should be noted that homologue sequences pre-existing on databases, such as any identified herein, may be excluded from one or more aspects or embodiments of the present invention while included in one or more other aspects.

Derivatives which retain common structural features can be fragments of protamine such as those disclosed herein. Fragments of protamine comprise individual domains thereof, as well as smaller polypeptides derived from the domains. Preferably, smaller polypeptides derived from protamine according to the invention define a single feature which is characteristic of protamine. Fragments may in theory be almost any size, as long as they retain one feature of protamine. Preferably, fragments will be between 5 and 20 amino acids in length. Longer fragments are regarded as truncations of the full-length protamine and generally encompassed by the term "protamine". Exemplary fragments of a protamine polypeptide include amino acid sequences extending from position 9 to position 18, from position 9 to position 20, from position 9 to position 21, from position 9 to position 22, from position 9 to position 23, from position 10 to position 20, from position 10 to position 21, from position 10 to position 22, from position 10 to position 23, and from position 10 to 24 of SEQ ID NO. 2.

Derivatives of protamine also comprise mutants thereof, which may contain amino acid deletions, additions or substitutions, subject to the requirement to maintain at least one feature characteristic of protamine. Thus, conservative amino acid substitutions may be made substantially without altering the nature of protamine, as may truncations from the 5' or 3' ends. Deletions and substitutions may moreover be made to the fragments of protamine comprised by the invention. Protamine mutants may be produced from a DNA encoding protamine which has been subjected to in vitro mutagenesis resulting e.g. in an addition, exchange and/or deletion of one or more amino acids. For example, substitutional, deletional or insertional variants of protamine can be prepared by recombinant methods and screened for immuno-crossreactivity with the native forms of protamine. Derivatives of protamine further comprise multimeric forms of protamine or functional fragments thereof.

The present invention also provides polypeptides and derivatives of protamine which retain at least one common antigenic determinant of protamine.

"Common antigenic determinant" means that the derivative in question possesses at least one antigenic function of protamine. Antigenic functions includes possession of an epitope or antigenic site that is capable of cross-reacting with antibodies raised against a naturally occurring or denatured protamine polypeptide or fragment thereof.

Derivatives which retain common antigenic determinants can be fragments of protamine. Fragments of protamine comprise individual domains thereof, as well as smaller polypeptides derived from the domains. Preferably, smaller polypeptides derived from protamine according to the invention define a single epitope which is characteristic of protamine. Fragments may in theory be almost any size, as long as they retain one characteristic of protamine. Preferably, fragments will be between 5 and 20 amino acids in length. Longer fragments are regarded as truncations of the full-length protamine and generally encompassed by the term "protamine". Derivatives of protamine further comprise multimeric forms of protamine or functional fragments thereof.

The present invention provides methods for recombinantly producing a protamine polypeptide comprising the steps of (a) expressing a polypeptide encoded by a DNA as outlined above in a suitable host, and (b) isolating said protamine polypeptide according to conventional techniques well known in the art. In addition, there is provided a protein which is obtained or obtainable by use of the aforementioned process.

Preferably, the protein or derivative thereof of the invention is provided in isolated form. "Isolated" means that the protein or derivative has been identified and is free of one or more components of its natural environment. Isolated protamine includes protamine in a recombinant cell culture. Protamine present in an organism expressing a recombinant protamine gene, whether the protamine protein is "isolated" or otherwise, is included within the scope of the present invention.

The host material selected for transformation should express the gene(s) introduced, and is preferably homozygous for expression thereof. Generally, the gene will be operably linked to a promoter functionally active in the targeted host cells of the particular plant, insect, animal or microorganism (such as e.g. fungi including yeast and bacteria). The expression should be at a level such that the characteristic desired from the gene is obtained. For example, the expression of a selectable marker gene should provide for an appropriate selection of transformants yielded according to the methods of the present invention. Similarly, the expression of a gene coding for an enzyme displaying the desired activity of protamine should result in a transformant having a relatively higher content of the encoded gene product as compared to that of the same species which is not subjected to the transformation method according to the present invention. On the other hand, it will generally be desired to limit the excessive expression of the gene of interest in order to avoid significantly adversely affecting the normal physiology of the plant, insect, fungal, animal or microorganism, i.e. to the extent that cultivation thereof becomes difficult.

The gene encoding protamine can be used in expression cassettes for expression in the transformed procaryotic or eucaryotic host cell, seed, tisue or whole organism. To achieve the objects of the present invention, i.e., to produce protamine in a target host of interest, the transformation is preferably carried out by use of an operable expression cassette comprising a transcriptional initiation region linked to the gene encoding protamine.

The transcriptional initiation may be native or analogous to the host or foreign or heterologous to the host. By foreign is intended that the transcriptional initiation region is not found in the wild-type host into which the transcriptional initiation region is introduced.

In plant material, those transcriptional initiation regions are of particular interest which are associated with storage proteins, such as glutelin, patatin, napin, cruciferin, β-conglycinin, phaseolin, or the like.

The transcriptional cassette will include, in 5'-3' direction of transcription, a transcriptional and translational initiation region, a DNA sequence encoding protamine or a functional fragment thereof retaining its specific immunogenic or biological activity, and a transcriptional and translational termination region functional in the targeted host material such as, e.g., plants or microorganims, respectively. The termination region may be native with the transcriptional initiation region, may be native with the DNA sequence of interest, or may be derived from other sources. Convenient termination regions suitable for plant material are available from the Ti-plasmid of *A. tumefaciens* such as the octopine synthase and nopaline synthase termination regions [see also, Guerineau et al., (1991) *Mol. Gen. Genet.* 262, 141-144; Proudfoot, (1991) *Cell* 64, 671-674; Sanfacon et al., (1991) *Gened Dev.* 5, 141-149; Mogen et al., (1990) *Plant Cell* 2, 1261-1272; Munroe et al., (1990) *Gene* 91, 151-158; Ballas et al., (1989), *Nucl. Acids Res.* 17, 7891-7903; Joshi et al., (1987) *Nucl. Acids Res.* 15, 9627-9639].

For the expression of protamine in plant or plastid-containing material, the coding sequence is preferably fused to a sequence encoding a transit peptide which after expression and translation directs the translocation of the protein upon cleavage of the transit peptide to (plant) plastids, such as chloroplasts. For example, the protamine cDNA can be translationally fused to a sequence encoding for the transit peptide of the small subunit of ribulose-1,5-bis-phosphate carboxylase (rubisco) or to sequences coding for transit peptides of other plastid proteins. Such transit peptides are known in the art [see, for example, Von Heijne et al., (1991) *Plant Mol. Biol. Rep.* 9, 104-126; Clark et al., (1989) *J. Biol. Chem.* 264, 17544-17550; Della-Cioppa et al., (1987) *Plant Physiol.* 84, 965-968; Romer et al., (1993) *Biochim Biophys. Res. Commun.* 196, 1414-1421; and, Shah et al., (1986) *Science* 233, 478-481]. Any genes useful for carrying out the present invention can utilize native or heterologous transit peptides.

The construct can also include any other necessary regulators such as plant translational consensus sequences (Joshi, 1987, s.a.), introns [Luehrsen and Walbot, (1991) *Mol. Gen. Genet.* 225, 81-93] and the like, operably linked to the nucleotide sequence encoding protamine. Intron sequences within the coding gene desired to be introduced may increase its expression level by stabilizing the transcript and allowing its effective translocation out of the nucleus. Among the known such intron sequences are the introns of the plant ubiquitin gene (Cornejo, *Plant Mol. Biol.* 23, 567-581, 1993). Furthermore, it has been observed that the same construct inserted at different loci on the genome can vary in the level of expression in plants. The effect is believed to be due at least in part to the position of the gene on the chromosome, i.e., individual isolates will have different expression levels (see, for example, Hoever et al., *Transgenic Res.* 3, 159-166, 1994). Further regulatory DNA sequences that may be used for the construction of expression cassettes include, for example, sequences that are capable of regulating the transcription of an associated DNA sequence in plant tissues in the sense of induction or repression.

There are, for example, certain plant genes that are known to be induced by various internal and external factors, such as plant hormones, heat shock, chemicals, pathogens, oxygen deficiency, light, stress, etc.

A further group of DNA sequences which can be regulated comprises chemically-driven sequences that are present, e.g., in the PR (pathogenesis-related) protein genes of tobacco and are inducible by means of chemical regulators such as those described in EP-A 0 332 104.

Yet another consideration in expression of foreign genes in plants, animals, insects, fungi or microorganims is the level of stability of the transgenic genome, i.e., the tendency of a foreign gene to segregate from the population. If a selectable marker is linked to the gene or expression cassette of interest, then selection can be applied to maintain the transgenic host organism or part thereof.

It may be beneficial to include 5' leader sequences in the expression cassette construct. Such leader sequences can act to enhance translation. Translation leaders are known in the art and include: picornavirus leaders, for example, EMCV leader (Encephalomyocarditis 5' noncoding region; Elroy-Stein et al., *Proc. Natl. Acad. Sci. USA* 86, 6126-6130, 1989); potyvirus leaders, for example, TEV leader (Tobacco Etch Virus; Allisson et al., *Virology* 154, 9-20, 1986); and human immunoglobulin heavy-chain binding protein (BiP, Macejak and Sarnow, *Nature* 353, 90-94, 1991); untranslated leader from the coat protein mRNA of alfalfa mosaic virus (AMV RNA 4; Jobling and Gehrke, *Nature* 325, 622-625, 1987); tobacco mosaic virus leader (TMV; Gallie et al., *Molecular Biology of RNA*, 237-256, 1989); and maize chlorotic mottle virus leader (MCMV; Lommel et al., *Virology* 81, 382-385, 1991; see also, Della-Cioppa et al., 1987, s.a.).

Depending upon where the DNA sequence encoding protamine is to be expressed, it may be desirable to synthesize the sequence with host preferred codons, or alternatively with chloroplast or plastid preferred codons. The plant preferred codons may be determined from the codons of highest frequency in the proteins expressed in the largest amount in the particular plant species of interest (see, EP-A 0 359 472; EP-A 0 386 962; WO 91/16432; Perlak et al., *Proc. Natl. Acad. Sci* 88, 3324-3328, 1991; and Murray et al., *Nucl. Acids. Res.* 17, 477-498, 1989). In this manner, the nucleotide sequences can be optimized for expression in any targeted host. It is recognized that all or any part of the gene sequence may be optimized or synthetic. That is, synthetic or partially optimized sequences may also be used. For the construction of chloroplast preferred genes, see U.S. Pat. No. 5,545,817.

Expression systems encoding protamine are useful for the study of protamine activity, particularly in the context of transgenic cells, tissues or animals. Preferred is a system in which protamine expression has been attenuated, particularly where this is achieved by means of transposon insertion. Mutant cells, tissues or animals according to the invention have impaired protamine expression. Especially those expression mutants in which expression is severely attenuated but not limited, are useful for the study of protamine activity. They show increased sensitivity to modulated interaction of putative upstream signalling agents with specific target domains of protamine, as well as modification of the downstream targets predicted to mediate its biological response. Thus, the invention also provides a method for assessing the ability of an agent to target protamine activity comprising exposing a protamine mutant as described herein to the agent, and judging the effect of the biological activity of protamine.

In preparing the transcription cassette, the various DNA fragments may be manipulated, so as to provide for the DNA sequences in the proper orientation and, as appropriate in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, or the like may be employed, where insertions, deletions or substitutions, e.g. transitions and transversions, may be involved.

The expression cassette carrying the cDNA or genomic DNA encoding native or mutant protamine is placed into an expression vector by standard methods. As used herein, vector (or plasmid) refers to discrete elements that are used to introduce heterologous DNA into cells for either expression or replication thereof. Selection and use of such vehicles are well within the skill of the artisan. Many vectors are available, and selection of an appropriate vector will depend on the intended use of the vector, i.e. whether it is to be used for DNA amplification or for DNA expression, the size of the DNA to be inserted into the vector, the type of host (plant, animal, insect, fungi or microorganism) to be transformed with the vector, and the method of introducing the expression vector into host cells. Each vector contains various components depending on its function (amplification of DNA or expression of DNA) and the host cell for which it is compatible. A typical expression vector generally includes, but is not limited to, prokaryotic DNA elements coding for a bacterial replication origin and an antibiotic resistance gene to provide for the growth and selection of the expression vector in the bacterial host; a cloning site for insertion of an exogenous DNA sequence, which in this context would code for a protamine polypeptide or functional fragment thereof; prokaryotic or eukaryotic DNA elements that control initiation of transcription of the exogenous gene, such as a promoter; and DNA elements that control the processing of transcripts, such as a transcription termination/polyadenylation sequence. It also can contain such sequences as are needed for the eventual integration of the vector into the chromosome of the targeted host.

If prokaryotes are selected for recombinant production of protamine, it is preferred to use an inducible promoter, such as for e.g. pelB (accession no. M17364) and ompT (accession no. X06903).

In a preferred embodiment, the expression vector also contains a gene encoding a selection marker such as, e.g. hygromycin phosphotransferase (van den Elzen et al., *Plant Mol. Biol.* 5, 299-392, 1985), which is functionally linked to a promoter. Additional examples of genes that confer antibiotic resistance and are thus suitable as selectable markers include those coding for neomycin phosphotransferase kanamycin resistance (Velten et al., *EMBO J.* 3, 2723-2730, 1984); the kanamycin resistance (NPT II) gene derived from Tn5 (Bevan et al., *Nature* 304, 184-187, 1983); the PAT gene described in Thompson et al., (*EMBO J.* 6, 2519-2523, 1987); and chloramphenicol acetyltransferase. For a general description of plant expression vectors and selectable marker genes suitable according to the present invention, see Gruber et al., [in: *Methods in Plant Molecular Biology and Biotechnology* 89-119 (CRC Press), 1993]. As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Suitable selectable markers for mammalian cells are those that enable the identification of cells competent to take up protamine nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes protamine. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

A promoter element employed to control expression of the gene of interest and the marker gene, respectively, can be any plant-compatible promoter. Those can be plant gene promoters, such as the promoter for the small subunit of ribulose-1,5-bis-phosphate carboxylase (RUBISCO), or promoters from tumour-inducing plasmids of *Agrobacterium tumefaciens*, like that nopaline synthase and octopine synthase promoters, or viral promoters such as the cauliflower mosaic virus (CaMV) 19S and 35S promoters or the figwort mosaic virus 35S promoter. See international application WO 91/19806, for example, for a review of known plant promoters which are suitable for use in the present invention.

According to a preferred embodiment, the cassette for the expression of protamine comprises the protamine encoding nucleic acid sequence translationally fused to a sequence encoding a transit peptide, e.g. for plastid import, polyadenylation signals and transcription terminators, each operably linked to a suitable constitutive, inducible or tissue-specific promoter which enables the expression of the desired protein in plant cells, seeds, tissues or in whole plants.

Moreover, the protamine gene according to the invention preferably includes a signal peptide, leader or secretion sequence in order to facilitate secretion of the polypeptide from bacterial hosts, such that it will be produced as a soluble native peptide rather than in an inclusion body. Examples for such leader sequences include pelB (accession no. M17364) and ompT (accession no. X06903). The peptide can be recovered from the bacterial periplasmic space, or the culture medium, as appropriate.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes coding for the alpha- or a-factor or a promoter derived from a gene encoding a glycolytic enzyme such as the promoter of the enolase, glyceraldehyde-3-phosphate dehydrogenase (GAP), 3-phospho-glycerate kinase (PGK), hexokinase, pyruvate decarboxylase, phosphofructokinase, glucose-6-phosphate isomerase, 3-phos-phoglycerate mutase, pyruvate kinase, triose phosphate isomerase, phosphoglucose isomerase or glucokinase genes, or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(S) of the yeast PH05 gene and downstream promoter elements including a functional TATA box of the yeast GAP gene (PH05-GAP hybrid promoter). A suitable constitutive PHO5 promoter is e.g. a shortened acid phosphatase PH05 promoter devoid of the upstream regulatory elements (UAS) such as the PH05 (−173) promoter element starting at nucleotide −173 and ending at nucleotide −9 of the PH05 gene.

Protamine gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with protamine sequence, provided such promoters are compatible with the host cell systems.

Transcription of a DNA encoding protamine by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100-270) and the CMV early promoter enhancer. The enhancer may be spliced into the vector at a position 5' or 3' to protamine DNA, but is preferably located at a site 5' from the promoter.

Advantageously, a eukaryotic expression vector encoding protamine can comprise a locus control region (LCR). LCRs are capable of directing high-level integration site independent expression of transgenes integrated into host cell chromatin, which is of importance especially where the protamine gene is to be expressed in the context of a permanently-transfected eukaryotic cell line in which chromosomal integration of the vector has occurred, in vectors designed for gene therapy applications or in transgenic animals or other hosts disclosed herein or known in the art.

According to a preferred embodiment of the present invention, the expression cassettes and plasmid or vector systems disclosed herein additionally comprise nucleic acid sequences which encode specific protamine modifying enzymes and/or protamine binding proteins, preferably being co-expressed with the polypeptide according to the invention, as already outlined above.

Suitable eukaryotic host cells for expression of protamine embrace fungi including yeast, insect, plant, animal, human, or nucleated cells from other multicellular organisms will also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding protamine.

The procaryotic or eucaryotic host cells, seeds, tissues and whole organisms contemplated in the context of the present invention may be obtained by any of several methods. Those skilled in the art will appreciate that the choice of method might depend on the type of host such as plant, i.e. monocot or dicot, targeted for transformation. Such methods generally include direct gene transfer, chemically-induced gene transfer, electroporation, microinjection (Crossway et al., *Bio-Techniques* 4, 320-334, 1986; Neuhaus et al., *Theor. Appl. Genet.* 75, 30-36, 1987), Agrobacterium-mediated gene transfer, ballistic particle acceleration using, for example, devices available from Agracetus, Inc., Madison, Wis., and Dupont, Inc., Wilmington, Del. (see, for example, Sanford et al., U.S. Pat. No. 4,945,050; and Mc Cabe et al., *Biotechnology* 6, 923-926, 1988), and the like.

When introducing a chosen gene construct into a cell, certain considerations must be taken into account, well, known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material either will or will not occur. Finally, as far as plants are concerned the target cell type may be such that cells can be regenerated into whole plants.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

One method for obtaining the present transformed plants or parts thereof is direct gene transfer in which plant cells are cultured or otherwise grown under suitable conditions in the presence of DNA oligonucleotides comprising the nucleotide sequence desired to be introduced into the plant or part thereof. The donor DNA source is typically a plasmid or other suitable vector containing the desired gene or genes. For convenience, reference is made herein to plasmids, with the understanding that other suitable vectors containing the desired gene are also contemplated.

Any suitable plant tissue which takes up the plasmid may be treated by direct gene transfer. Such plant tissue includes, for example, reproductive structures at an early stage of development, particularly prior to meiosis, and especially 1-2 weeks pre-meiosis. Generally, the pre-meiotic reproductive organs are bathed in plasmid solution, such as, for example, by injecting plasmid solution directly into the plant at or near the reproductive organs. The plants are then self-pollinated, or cross-pollinated with pollen from another plant treated in the same manner. The plasmid solution typically contains about 10-50 μg DNA in about 0.1-10 ml per floral structure, but more or less than this may be used depending on the size of the particular floral structure. The solvent is typically sterile water, saline, or buffered saline, or a conventional plant medium. If desired, the plasmid solution may also contain agents to chemically induce or enhance plasmid uptake, such as, for example, PEG, $Ca^{2+}$ or the like.

Following exposure of the reproductive organs to the plasmid, the floral structure is grown to maturity and the seeds are harvested. Depending on the plasmid marker, selection of the transformed plants with the marker gene is made by germination or growth of the plants in a marker-sensitive, or preferably a marker-resistant medium. For example, seeds obtained from plants treated with plasmids having the kanamycin resistance gene will remain green, whereas those without this marker gene are albino. Presence of the desired gene transcription of mRNA therefrom and expression of the peptide can further be demonstrated by conventional Southern, northern, and western blotting techniques.

All plant transformation systems produce a mixture of transgenic and non-transgenic plants. The selection of transgenic plant cells can be accomplished by the introduction of an antibiotic or herbicide gene, enabling the transgenic plant cells to be selected on media containing the corresponding toxic compound. Besides those marker systems for the selection of transgenic plants new so-called "positive selection systems" have been successfully used for plant transformation (PCT/EP94/00575, WO94/20627). In contrast to antibiotic or herbicide resistance selection systems in which transgenic cells acquire the ability to survive on a selection medium while non-transgenic cells are killed, this method favours regeneration and growth of the transgenic plant cells while non-transgenic plant cells are starved, but not killed. Therefore, this selection strategy is termed "positive selection". Vector systems for Agrobacterium-mediated transformation have been constructed and have been successfully used e.g. to transform potato, tobacco and tomato and are described e.g. by Haldrup, A., Petersen S. G. and Okkels F. T. [Plant Mol. Biol. 37, pp. 287-296, (1998)]. Transformation systems based on this positive selection systems can be used according to the invention to introduce constructs harbouring protamine to obtain plants expressing the protamine polypeptide or functional fragment thereof. In addition, the use of those selection systems would have the advantage to overcome disadvantages in using antibiotic or herbicide genes in a selection system such as e.g. toxicity or allergenicity of the gene product and interference with antibiotic treatment, as generally known in the art.

The list of possible transformation methods given above by way of example is not claimed to be complete and is not intended to limit the subject of the invention in any way.

The present invention therefore also comprises a procaryotic or eucaryotic host cell, seed, tissue or whole organism transformed or transfected with the DNA molecule or with the plasmid or vector system according to the invention as set out hereinbefore in a manner enabling said host cell, seed, tissue or whole organism to express a polypeptide or functional fragment thereof having the biological activity of protamine and/or having the capability of specifically binding to antibodies raised against said polypeptide or functional fragment thereof.

According to the invention, the procaryotic or eucaryotic host cell, seed, tissue or whole organism is selected from the group consisting of bacteria, yeast, fungi, insect, animal and plant cells, seeds, tissues or whole organisms. As for the procaryotic taxonomic groups, the host can be selected from the group consisting of proteobacteria including members of the alpha, beta, gamma, delta and epsilon subdivision, gram-positive bacteria including *Actinomycetes, Firmicutes, Clostridium* and relatives, flavobacteria, cyanobacteria, green sulfur bacteria, green non-sulfur bacteria, and archaea. Suitable proteobacteria belonging to the alpha subdivision can be selected from the group consisting of *Agrobacterium, Rhodospirillum, Rhodopseudomonas, Rhodobacter, Rhodomicrobium, Rhodopila, Rhizobium, Nitrobacter, Aquaspirillum, Hyphomicrobium, Acetobacter, Beijerinckia, Paracoccus* and *Pseudomonas*, with *Rhodopseudomonas* and *Pseudomonas* being preferred and *Rhodopseudomonas palustris* and *Pseudomonas fluorescens*, respectively, being most preferred. Suitable proteobacteria belonging to the beta subdivision can be selected from the group consisting of *Rhodocyclus, Rhodopherax, Rhodovivax, Spirillum, Nitrosomonas, Spherotilus, Thiobacillus, Alcaligenes, Pseudomonas, Bordetella* and *Neisseria*, with ammonia-oxidizing bacteria such as *Nitrosomonas* being preferred and *Nitrosomonas* sp. ENI-11 being most preferred. Suitable proteobacteria belonging to the gamma subdivision can be selected from the group consisting of *Chromatium, Thiospirillum, Beggiatoa, Leucothrix, Escherichia* and *Azotobacter*, with *Enterobacteriaceae* such as *Escherichia coli* being preferred, and with *E. coli* K12 strains such as e.g. M15 (described as DZ 291 by Villarejo et al. in J. Bacteriol. 120, 466-474, 1974), HB 101 (ATCC No. 33649) and *E. coli* SG13009 (Gottesman et al., J. Bacteriol. 148, 265-273, 1981) being most preferred. Suitable proteobacteria belonging to the delta subdivision can be selected from the group consisting of *Bdellovibrio, Desulfovibrio, Desulfuromonas* and *Myxobacteria* such as *Myxococcus*, with *Myxococcus xanthus* being preferred. Suitable proteobacteria belonging to the epsilon subdivision can be selected from the group consisting of *Thiorulum, Wolinella* and *Campylobacter*. Suitable gram-positive bacteria can be selected from the group consisting of *Actinomycetes* such as *Actinomyces, Bifidobacterium, Propionibacterium, Streptomyces, Nocardia, Actinoplanes, Arthrobacter, Coryne-bacterium, Mycobacterium, Micromonospora, Frankia, Cellulomonas* and *Brevibacterium*, and *Firmicutes* including *Clostridium* and relatives such as *Clostridium, Bacillus, Desulfotomaculum, Thermoactinomyces, Sporosarcina, Acetobac-terium, Streptococcus, Enterococcus, Peptococcus, Lacto-bacillus, Lactococcus, Staphylococcus, Rominococcus, Plano-coccus, Mycoplasma, Acheoleplasma* and *Spiroplasma*, with *Bacillus subtilis* and *Lactococcus lactis* being preferred. Suitable flavobacteria can be selected from the group consisting of *Bacteroides, Cytophaga* and *Flavobacterium*, with *Flavobacterium* such as *Flavobacterium* ATCC21588 being preferred. Suitable cyanobacteria can be selected from the group consisting of *Chlorococcales* including *Synecho-cystis* and *Synechococcus*, with *Synechocystis* sp. and *Synechococcus* sp. PS717 being preferred. Suitable green sulfur bacteria can be selected from the group *Chlorobium*, with *Chlorobium limicola f. thiosulfatophilum* being preferred. Suitable green non-sulfur bacteria can be selected from the group *Chloroflexaceae* such as *Chloroflexus*, with *Chloroflexus aurantiacus* being preferred. Suitable archaea can be selected from the group of *Halobacteriaceae* including *Halobacterium*, with *Halobacterium salinarum* being preferred.

As for the eucaryotic taxonomic group of fungi including yeast, the host can be selected from the group consisting of *Ascomycota* including *Saccharomycetes* such as *Pichia* and *Saccharomyces*, and anamorphic *Ascomycota* including *Aspergillus*, with *Saccharomyces cerevisiae* and *Aspergillus niger* (e.g. ATCC 9142) being preferred.

The eucaryotic host system comprises insect cells which preferably are selected from the group consisting of SF9, SF21, Trychplusiani and MB21. For example, the polypeptides according to the invention can advantageously be expressed in insect cell systems. Insect cells suitable for use in the method of the invention include, in principle, any lepidopteran cell which is capable of being transformed with an expression vector and expressing heterologous proteins encoded thereby. In particular, use of the Sf cell lines, such as the *Spodoptera frugiperda* cell line IPBL-SF-21 AE (Vaughn et al., (1977) In Vitro 13, 213-217) is preferred. The derivative cell line Sf9 is particularly preferred. However, other cell lines, such as *Tricoplusia ni* 368 (Kurstack and Marmorosch, (1976) Invertebrate Tissue Culture Applications in Medicine, Biology and Agriculture. Academic Press, New York, USA) can be employed. These cell lines, as well as other insect cell lines suitable for use in the invention, are commercially available (e.g. from Stratagene, La Jolla, Calif., USA). As well as expression in insect cells in culture, the invention also comprises the expression of heterologous proteins such as protamine in whole insect organisms. The use of virus vectors such as baculovirus allows infection of entire insects, which are in some ways easier to grow than cultured cells as they have fewer requirements for special growth conditions. Large insects, such as silk moths, provide a high yield of heterologous protein. The protein can be extracted from the insects according to conventional extraction techniques. Expression vectors suitable for use in the invention include all vectors which are capable of expressing foreign proteins in insect cell lines. In general, vectors which are useful in mammalian and other eukaryotic cells are also applicable to insect cell culture. Baculovirus vectors, specifically intended for insect cell culture, are especially preferred and are widely obtainable commercially (e.g. from Invitrogen and Clontech). Other virus vectors capable of infecting insect cells are known, such as Sindbis virus (Hahn et al., (1992) PNAS (USA) 89, 2679-2683). The baculovirus vector of choice (reviewed by Miller (1988) Ann. Rev. Microbiol. 42, 177-199) is *Autographa californica* multiple nuclear polyhedrosis virus, AcMNPV. Typically, the heterologous gene replaces at least in part the polyhedrin gene of AcMNPV, since polyhedrin is not required for virus production. In order to insert the heterologous gene, a transfer vector is advantageously used. Transfer vectors are prepared in *E. coli* hosts and the DNA insert is then transferred to AcMNPV by a process of homologous recombination.

The eucaryotic host sytem further comprises animal cells preferably selected from the group consisting of Baby Hamster Kidney (BHK) cells, Chinese Hamster Ovarian (CHO) cells, Human Embryonic Kidney (HEK) cells and COS cells, with NIH 3T3 and 293 being most preferred.

The host cells referred to in this disclosure comprise cells in in vitro culture as well as cells that are within a host organism.

The present invention also provides transgenic plant material, selected from the group consisting of protoplasts, cells, calli, tissues, organs, seeds, embryos, ovules, zygotes, etc. and especially, whole plants, that has been transformed by means of the method according to the invention and comprises the recombinant DNA of the invention in expressible form, and processes for the production of the said transgenic plant material.

In accordance with yet another embodiment of the present invention, there are provided antibodies specifically recognising and binding to protamine. For example, such antibodies may be generated against a protamine polypeptide species having any of the amino acid sequences as set forth in SEQ ID NOS. 2, 4, 6, 8, 10, 12, 14, 16, 18, 20, 22, 24, and 34. Alternatively, protamine or protamine fragments (which may also be synthesised by in vitro methods), such as those described hereinbefore, are fused (by recombinant expression or an in vitro peptidyl bond) to an immunogenic polypeptide, and this fusion polypeptide, in turn, is used to raise antibodies against a protamine epitope.

Anti-protamine antibodies may be recovered from the serum of immunised animals. Monoclonal antibodies may be prepared from cells from immunised animals in the conventional manner. The antibodies of the invention are useful for studying protamine localisation, screening of an expression library to identify nucleic acids encoding protamine or the structure of functional domains, as well as for the purification of protamine, and the like.

Antibodies according to the invention may be whole antibodies of natural classes, such as IgE and IgM antibodies, but are preferably IgG antibodies. Moreover, the invention includes antibody fragments, such as Fab, $F(ab')_2$, Fv and ScFv. Small fragments, such Fv and ScFv, possess advantageous properties for diagnostic and therapeutic applications on account of their small size and consequent superior tissue distribution.

The antibodies according to the invention are especially indicated for diagnostic and therapeutic applications.

Accordingly, they may be altered antibodies comprising an effector protein such as a toxin or a label. Especially preferred are labels which allow the imaging of the distribution of the antibody in a tumour in vivo. Such labels may be radioactive labels or radioopaque labels, such as metal particles, which are readily visualisable within the body of a patient. Moreover, the may be fluorescent labels or other labels which are visualisable on tissue samples removed from patients. In addition, said antibodies can also be used for purifying protamine from native sources or from transformed host cells or culture medium.

Recombinant DNA technology may be used to improve the antibodies of the invention. Thus, chimeric antibodies may be constructed in order to decrease the immunogenicity thereof in diagnostic or therapeutic applications. Moreover, immunogenicity may be minimised by humanising the antibodies by CDR grafting [see EP-A 0 239 400 (Winter)] and, optionally, framework modification [see WO 90/07861 (Protein Design Labs)].

Antibodies according to the invention may be obtained from animal serum, or, in the case of monoclonal antibodies or fragments thereof, produced in cell culture. Recombinant DNA technology may be used to produce the antibodies according to established procedure, in bacterial or preferably mammalian cell culture. The selected cell culture system preferably secretes the antibody product.

Therefore, the present invention includes a process for the production of an antibody according to the invention comprising culturing a host, e.g. *E. coli* or a mammalian cell, which has been transformed with a hybrid vector comprising an expression cassette comprising a promoter operably linked to a first DNA sequence encoding a signal peptide linked in the proper reading frame to a second DNA sequence encoding the antibody, and isolating said antibody.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. fetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The cell culture supernatants are screened for the desired antibodies, preferentially by immunofluorescent staining of cells expressing protamine, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-)affinity chromatography, e.g. affinity chromatography with protamine protein or with Protein-A.

The invention further concerns hybridoma cells secreting the monoclonal antibodies of the invention. The preferred hybridoma cells of the invention are genetically stable, secrete monoclonal antibodies of the invention of the desired specificity and can be activated from deep-frozen cultures by thawing and recloning.

The invention also concerns a process for the preparation of a hybridoma cell line secreting monoclonal antibodies directed against protamine, characterised in that a suitable mammal, for example a Balb/c mouse, is immunised with purified protamine protein, an antigenic carrier containing purified protamine or with cells bearing protamine, antibody-producing cells of the immunised mammal are fused with cells of a suitable myeloma cell line, the hybrid cells obtained in the fusion are cloned, and cell clones secreting the desired antibodies are selected. For example spleen cells of Balb/c mice immunised with cells bearing protamine are fused with cells of the myeloma cell line PAI or the myeloma cell line Sp2/0-Ag14, the obtained hybrid cells are screened for secretion of the desired antibodies, and positive hybridoma cells are cloned.

Preferred is a process for the preparation of a hybridoma cell line, characterised in that Balb/c mice are immunised by injecting subcutaneously and/or intraperitoneally between 10 and $10^7$ and $10^8$ cells of human tumour origin which express protamine containing a suitable adjuvant several times, e.g. four to six times, over several months, e.g. between two and four months, and spleen cells from the immunised mice are taken two to four days after the last injection and fused with cells of the myeloma cell line PAI in the presence of a fusion promoter, preferably polyethylene glycol. Preferably the myeloma cells are fused with a three- to twentyfold excess of spleen cells from the immunised mice in a solution containing about 30% to about 50% polyethylene glycol of a molecular weight around 4000. After the fusion the cells are expanded in suitable culture media as described hereinbefore, supplemented with a selection medium, for example HAT medium, at regular intervals in order to prevent normal myeloma cells from overgrowing the desired hybridoma cells.

The invention also concerns recombinant DNAs comprising an insert coding for a heavy chain variable domain and/or for a light chain variable domain of antibodies directed to the protamine protein. By definition such DNAs comprise coding single stranded DNAs, double stranded DNAs consisting of said coding DNAs and of complementary DNAs thereto, or these complementary (single stranded) DNAs themselves.

Furthermore, DNA encoding a heavy chain variable domain and/or for a light chain variable domain of antibodies directed against protamine can be enzymatically or chemically synthesised DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted or exchanged with one or more other amino acids. Preferably said modification(s) are outside the CDRs of the heavy chain variable domain and/or of the light chain variable domain of the antibody. Such a mutant DNA is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly *E. coli*, to obtain an optimal expression of the heavy chain murine variable domain and/or a light chain murine variable domain.

The term "mutant" is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

In the case of a diagnostic composition, the antibody is preferably provided together with means for detecting the antibody, which may be enzymatic, fluorescent, radioisotopic or other means. The antibody and the detection means may be provided for simultaneous, simultaneous separate or sequential use, in a diagnostic kit intended for diagnosis.

In a further aspect of the invention there is provided a pharmaceutical composition comprising a bioactive protamine protein, peptide or a functionally equivalent molecule or a combination thereof displaying protamine activity, and optionally a pharmaceutically acceptable carrier or excipient. Compositions comprising such carriers can be formulated by well known conventional methods.

For parenteral administration, the protamine proteins, polypeptides or functional fragments thereof (as defined herein) can be, for example, formulated as a solution, suspension, or lyophilised powder in association with a pharmaceutically acceptable parenteral vehicle. Examples of such vehicles are water, saline, Ringer's solution, dextrose solution, and 5% human serum albumin. The vehicle or lyophilised powder may contain additives that maintain isotonicity (e.g. sodium chloride, mannitol) and chemical stability (e.g. buffers and preservatives). For example, a parenteral composition suitable for administration by injection may be prepared by dissolving 1.5% by weight of active ingredient in 0.9% sodium chloride solution. The formulation may be sterilised by any commonly used technique.

The pharmaceutical composition according to the invention may be administered as a single dose or in multiple doses. The said compositions may be administered either as individual therapeutic agents or in combination with each other or with other therapeutic agents. The treatments of the present invention may be combined with conventional therapies which may be administered sequentially or simultaneously.

The pharmaceutical compositions of the invention may be administered by any means that enables the active protamine protein component to reach the targeted cells. Since compounds of the invention may be susceptible to digestion enzymes found in the lumen and/or linings of the gut, when administered orally, parenteral administration i.e. via intravenous, subcutaneous, or intramuscular would appear to be the preferred route of administration. Intravenous administration may be accomplished with the aid of an infusion pump. Alternatively, the protamine protein component can be formulated as aerosol medicaments for intranasal inhalation.

The dosage required varies depending on factors such as pharmacodynamic characteristics; its mode and route of administration; age; health; and weight of the recipient; nature and extent of symptoms; type of concurrent treatment; and frequency of treatment. The dosage of the protamine component may be from 1 to 3000 mgs/50 kg of body weight; from 10 to 1000 mgs/50 kg of body weight; 25 to 800 mgs/50 kg of body weight, depending on the circumstances of the recipient in need of treatment thereof.

In a further aspect of the invention, the pharmaceutical composition comprising a protamine protein, peptide or a functionally equivalent molecule or a combination thereof additionally may comprise an anti-viral drug. Such a combination may further enhance the effectiveness of compositions of the invention and/or reduce undesired side effects. Examples of suitable anti-viral drugs are described, for example, by Flechter, Am. J. Hosp. Pharm. 51 (1994), 2251-2267 and by Stein et al., Clin. Inf. Dis. 17 (1993), 749-771.

A further embodiment of the present invention is the use of a protamine protein, peptide or a functionally equivalent molecule or a combination thereof for the preparation of a pharmaceutical composition for the prophylaxis or the treatment of diseases or malfunctions associated with heparin or insulin binding. Included in this aspect of the invention is the use of said protamine protein, peptide or a functionally equivalent molecule or a combination thereof in combination with an additional active ingredient.

According to a further aspect, the present invention relates to a composition capable of killing microbial cells or inhibiting growing microbial cells, i.e. bacteriocidal, bacteriostatic, fungicidal and/or fungistatic composition, which can be used for killing or inhibiting microbial cells present on a hard surface, on skin or in laundry, and for preserving food products, cosmetics, etc. Accordingly, the present invention provides a cleaning, detergent or disinfecting composition.

As discussed before, disinfectant formulations often contain harmful additives like Tris-hydroxymethyl-aminomethane (Tris) or Ethylene-diamine-tetra-acetic acid (EDTA). These substances are known to enhance the permeability of bacterial membranes or to form complexes with divalent cations which are necessary for the stabilization of the bacterial cell wall (VAARA 1992).

For purposes such as disinfection of small or large surfaces, e.g. food, laboratory benches, clinicical apparatus, floors or rooms including areas for keeping livestock, traces of these harmful compounds remain on the surfaces. Contact with them e.g. by touching, inhalating and/or swallowing can cause short or long term indisposition and/or illness in animals and humans beings.

Ecological as well as economical reasons demand the development of harmless substances and disinfectant formulations. A first step towards a sustainable product development is the awareness that biological and harmless defense systems particularly against bacteria exist, e.g. in the human eye. Hence, these systems have been adapted to their purpose.

In the course of experiments which have lead to the present invention, a harmless biological buffer system was developed on the basis of human tear electrolyte components containing the minimum number of compounds while causing a maximum effect, i.e. enhancing bacterial permeability.

Furthermore, we studied the bactericidal effect of protamine in combination with the developed biological buffer system on gram-positive and gram-negative bacteria. The bactericidal effect was studied on bacteria grown in rich medium in contrast to previous studies mainly using minimal medium.

The results of our studies will be discussed with respect to other publications on the inhibitory effect of protamine in minimal medium. Additional factors, e.g. the impact of pH-value alterations and the impact of natural permeabilizing substances will also be referred to.

According to the invention, harmless compounds displaying the desired activity, i.e. enhancing-bacterial permeability, were identified by testing modified human tear electrolytes. The respective experiments conducted have lead to the definition of compositions having the afore-mentioned effect or activity. Due to their potential- of killing microbial cells or inhibiting growing microbial cells the compositions provided by the present invention are suitable as cleaning or detergent compositions and can be used whenever it is desired to exert a bacteriocidal, bacteriostatic, fungicidal and/or fungistatic effect. It is clear for a person skilled in the art that there is a very broad range of application fields including, but not limited to, preparation and storage of food and food constituents, beverages, cosmetics and pharmaceuticals, medicinal and veterinary purposes, disinfection of surfaces and articles. The respective compounds as well as their absolute and relative amounts and concentrations can easily be selected in view of the specific application.

Accordingly, the present invention provides a bacteriocidal, bacteriostatic, fungicidal and/or fungistatic composition comprising or consisting essentially of citrate and bicarbonate. The component citrate includes citrate acid and salts of citrate in their hydrated forms such as trisodium salt of citric acid dihydrate. Similarly, the component bicarbonate includes carbonic acid and salts of mono- or bicarbonate such as sodium bicarbonate.

AYRES et al. (1999) demonstrated that citric acid is an effective permeabilizer of bacterial membranes and enhances the efficiency of several antibiotics. Citric acid is a natural substance, cheap and easy to store, and degradable.

As a further component phosphate may be comprised inlcuding phoshoric acid and salts of phosphate like sodium phosphate.

According to another preferred embodiment, the composition additionally comprises a basic protein or peptide selected from the group consisting of protamines, protamine sulphates, defensins, magainins, mellitin, cecropins and protegrins, with protamines and protamine sulphates being particularly preferred.

A suitable biologically active protamine or functional fragment thereof can be selected from the group consisting of proteins, polypeptides or peptides representing or comprising amino acid sequences extending from position 9 to position 18, from position 9 to position 20, from position 9 to position 21, from position 9 to position 22, from position 9 to position 23, from position 10 to position 20, from position 10 to position 21, from position 10 to position 22, from position 10 to position 23, and from position 10 to 24 of SEQ ID NO. 2; amino acid sequences as set out in SEQ ID NOS. 2, 4, 6, 8, 10, 12, 14, 16, 18, 20, 22, 24, and 26; amino acid sequences derived from SEQ ID NO. 33; amino acid sequences being encoded by nucleic acid sequences as set out in SEQ ID NOS. 1, 3, 5, 7, 9, 11, 13, 15, 17, 19, 21, 23, and 25; and amino acid sequences being encoded by nucleic acid sequences as set out in SEQ ID NOS. 27, 28, 29, 30, 31, and 32.

According to a further aspect, the composition further comprises lysozyme or any other substance known to degrade the cell wall of bacteria.

In the afore-mentioned compositions, it is preferred that the components citrate and bicarbonate are present in a molar ratio of 4:1, and that their preferred amounts are at least 0.04 M and 0.01 M, respectively. It should be understood that the amount of each component may generally vary from 0.01 to 0.4 Mol or even higher, depending on the envisaged field of application. Accordingly, the compositions may comprise more than 0.04 Mol citrate, preferably 0.2 Mol citrate, more preferably 0.4 Mol citrate, and more than 0.01 Mol bicarbonate, preferably 0.05 Mol, more preferably 0.1 Mol bicarbonate. The skilled artisan is able to calculate the weight in gram in order to obtain the desired composition.

In the case of a composition which additionally comprises phosphate, it is preferred that the components citrate, bicarbonate and phosphate are present in a molar ratio of 2:1:1, and that their preferred amounts are at least 0.2 M, 0.1 M and 0.1 M, respectively.

If the composition comprises a basic protein or peptide, it is preferred that this component is present in an amount of at least 0.1 µg. In case of using lysozyme or any other cell-wall degrading substance, it is preferred that this component is present in an amount of at least 0.1 µg.

For a broad range of applications, it may be desired to use the compositions according to the invention in liquid form (solution), e.g. by dissolving the components in water or other useful solvents and/or admixing prefabricated or stock solutions each comprising one or more of the compounds in a suitable concentration. Accordingly, the present invention provides such compositions in liquid form, which, in the case of citrate and bicarbonate being the components of choice, may be obtained by admixing an at least 0.01 mol/l citrate solution adjusted to pH 6.0 to 7.0 with an at least 0.01 mol/l bicarbonate solution in a ratio of 4:1 (vol./vol.).

An effect was observed when a solution comprising citrate at a pH of 7.0 was mixed with a solution comprising bicarbonate. The ph shifted to about 9.5 and the solution caused a baceriocidal/fungicidal effect. This effect could also be shown when mixing a solution of citrate with a pH of 6.2 with a solution comprising bicarbonate causing rise of the pH to about 8.0. Thus, the preferred pH for the citrate solution before mixing ranges between 6.0 and 7.0. In a preferred embodiment of the invention the solution after mixing comprises 0.4 mol/l citrate and 0.1 mol/l bicarbonate at a pH of 8.0 to 9.5.

In the case of phosphate being additionally selected as active component, said solution may be obtained by admixing an at least 0.01 mol/l citrate solution adjusted to pH 6.0 to 7.0 with an at least 0.01 mol/l bicarbonate solution and an at least 0.01 mol/l phosphate solution adjusted to ph 6.0 to 7.0 in a ratio of 2:1:1 (vol./vol.).

The effects mentioned above could also be observed when mixing a solution of citrate with a pH of 7.0 with a solution comprising bicarbonate and a solution comprising phosphate with a pH of 7.0. The pH shifted to about 10.0 and the solution caused a bacteriocidal/fungicidal effect.

Similar effects were observed when mixing a solution of at least 0.02 mol/l citrate with a pH of 6.2 with a solution comprising at least 0.01 mol/l bicarbonate and a solution comprising at least 0.01 mol/l phosphate with a pH of 6.2. The pH of the final solution shifted to about 8.0 and the solution caused a bacteriostatic/fungistatic effect.

In a preferred embodiment of the invention the final solution comprises 0.2 mol/l citrate and 0.1 mol/l bicarbonate and 0.1 mol/l phosphate at a pH ranging from about 7.0 to about 10.0.

If it is desired to include any basic protein such as protamine, it is preferred that the concentration of said basic protein such as protamine in said solution is at least 0.1 μg/ml. The same concentration is preferred for lysozyme or any other substance known to degrade the cell wall of bacteria.

An even more bacteriostatic/fungistatic and/or bacteriocidal/fungicidal effect was achieved by adding protamine and/or lysozyme to the solution. As less than 0.1 μg/ml protamine and/or lysozyme in a solution comprising citrate and bicarbonate and/or phosphate causes, a synergistic bacteriostatic/fungistatic and/or bacteriocidal/fungicidal effect. As a solution comprising citrate, bicarbonate and/or phosphate inhibits the growth of microorganisms and/or fungi or even kills them this capacity is enhanced by adding protamine and/or lysozyme. For example, if it is desired to treat small surfaces the concentration of citrate, bicarbonate and/or phosphate can be decreased by increasing the concentration of protamine and/or lysozyme without loss of a bacteriostatic/fungistatic and/or bacteriocidal/fungicidal effect. For treatment of larger surfaces the concentration of citrate, bicarbonate and/or phosphate can be increased by decreasing the concentration of protamine and/or lysozyme. This might be desired for economical and/or ecological reasons, because use of protamine or lysozyme in high amounts increases the costs.

In a preferred embodiment of the invention the compositions in liquid form (solution) comprise 0.4 mol/l citrate and 0.1 mol/l bicarbonate and 0.1 to 100 μg/ml protamine.

In an even more preferred embodiment of the invention the solution comprises 0.4 mol/l citrate and 0.1 mol/l bicarbonate at a pH of 8.0 to 9.5 and 0.1 to 10 μg/ml protamine and/or lysozyme.

In a preferred embodiment of the invention the solution comprises 0.2 mol/l citrate and 0.1 mol/l bicarbonate and/or 0.1 mol/l phosphate and 0.1 to 100 μg/ml protamine.

In an even more preferred embodiment of the invention the solution comprises 0.2 mol/l citrate and 0.1 mol/l bicarbonate and/or 0.1 mol/l phosphate at a pH of 8.0 to 10.0 and 0.1 to 10 μg/ml protamine and/or lysozyme.

BRIEF DESCRIPTION OF THE FIGURES

The application file contains at least one drawing executed in color. Copies of this patent application publication with color drawings will be provided by the Patent and Trademark Office upon request and payment of the necessary fee.

Embodiments and examples relating to the present invention are now described by way of example only with reference to the following figures.

FIG. 3 shows the effect of single components (citrate or bicarbonate) of the composition as well as in combination and in the presence of different concentrations of protamine on the growth of *Escherichia coli* DH5αa.

Figure 1:
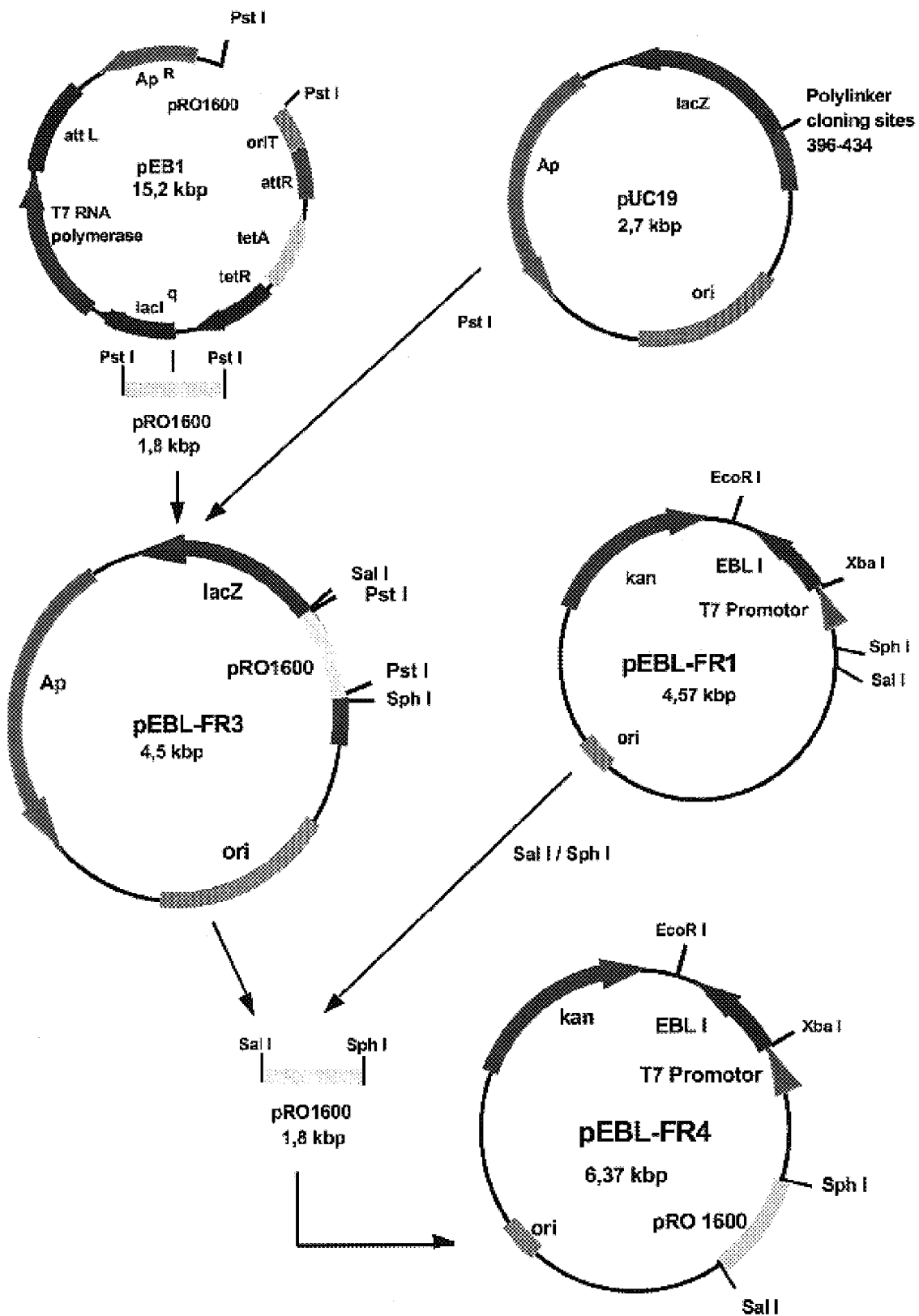
FIGS. 1 and 2 show how plasmids or vectors for use in the method according to the invention have been constructed. A more detailed description is given hereinbelow.

The initial bacterial inoculum was $10^7$ CFU/ml. Results are mean various of three independent experiments. The results show clearly that the combination of the above two components is capable of killing the bacteria tested. In contrast, the single components do not cause the same effect. At a pH of 8.0 it is necessary for the composition to additionally comprise protamine to achieve bacterial death. The further addition of lysozyme causes also bacterial death, however, the concentration of protamine needed is lowered to 30%.

Deposition of Biological Material

Suitable bacterial strains for carrying out the method according to the present invention have been deposited under the Budapest Treaty with the Deutsche Sammlung von Mikroorganismen und Zellkulturen (DSMZ) in Braunschweig, Germany, under the following Accession Nos.:

| Strain | Accession No. |
| --- | --- |
| *Escherichia coli* TAD1 | DSM 15050 |
| *Pseudomonas fluorescens* TAD2 | DSM 15051 |
| *Rhodopseudomonas palustris* TAD3 | DSM 15052 |

EXAMPLES (SECTION I)

1. Construction of the Coding Region of the Protamine Gene

Protamine is a peptide which occur in Salmon spermatozoon and have antimicrobial properties against bacteria and fungi (1,2,3). Some of the coding sequences and the gene product are well known (4).

To express protamine in bacteria a new gene have to be constructed because salmon have a different codon usage than bacteria; for example in salmon 9 of 21 arginies are coded by AGA and AGG, codons which were very rarely used in *E. coli*.

Therefore, a new gene was constructed under consideration of the codon usage of *Pseudomonas fluorescens* and *Escherichia coli* to ensure a optimal synthesis of the protamine peptide in bacteria. The elected sequence EBLI is shown in SEQ ID NO. 32.

The deduced amino acid sequence corresponds to the intact protamine, e.g. as set forth in SEQ ID NO. 2.

Our strategy was to express the protamine peptide in the periplasmic space of procaryotes. To realize this strategy the structure gene of EBLI was fused with an appropriate DNA sequence which codes for a leader peptide that targets the EBL peptide in the periplasmic space. Therefore, we used the leader sequence of the pelB gene (5, 6; SEQ ID NO. 34). After translocation of the peptide in the periplasmic space the leader sequence is removed by a signal peptidase.

To ensure that the mRNA is efficiently translated a ribosome binding site (AGGAG) was inserted upstream of the coding region. For the sequence and distances between promoter, ribosome binding site and the start codon ATG we utilised the data from the expression vector pET9a (6).

To clone the sequence in an expression vector we fused the sequence with the restriction sites for XbaI and BamHI. This whole construct was synthesised (cf. SEQ ID NO. 34).

2. Cloning of the Synthesised EBLI Construct in the Expression Vector pET9a

The expression vector pET9a was constructed for the expression of genes in special *E. coli* strains, which produce T7 polymerase.

Figure 2:
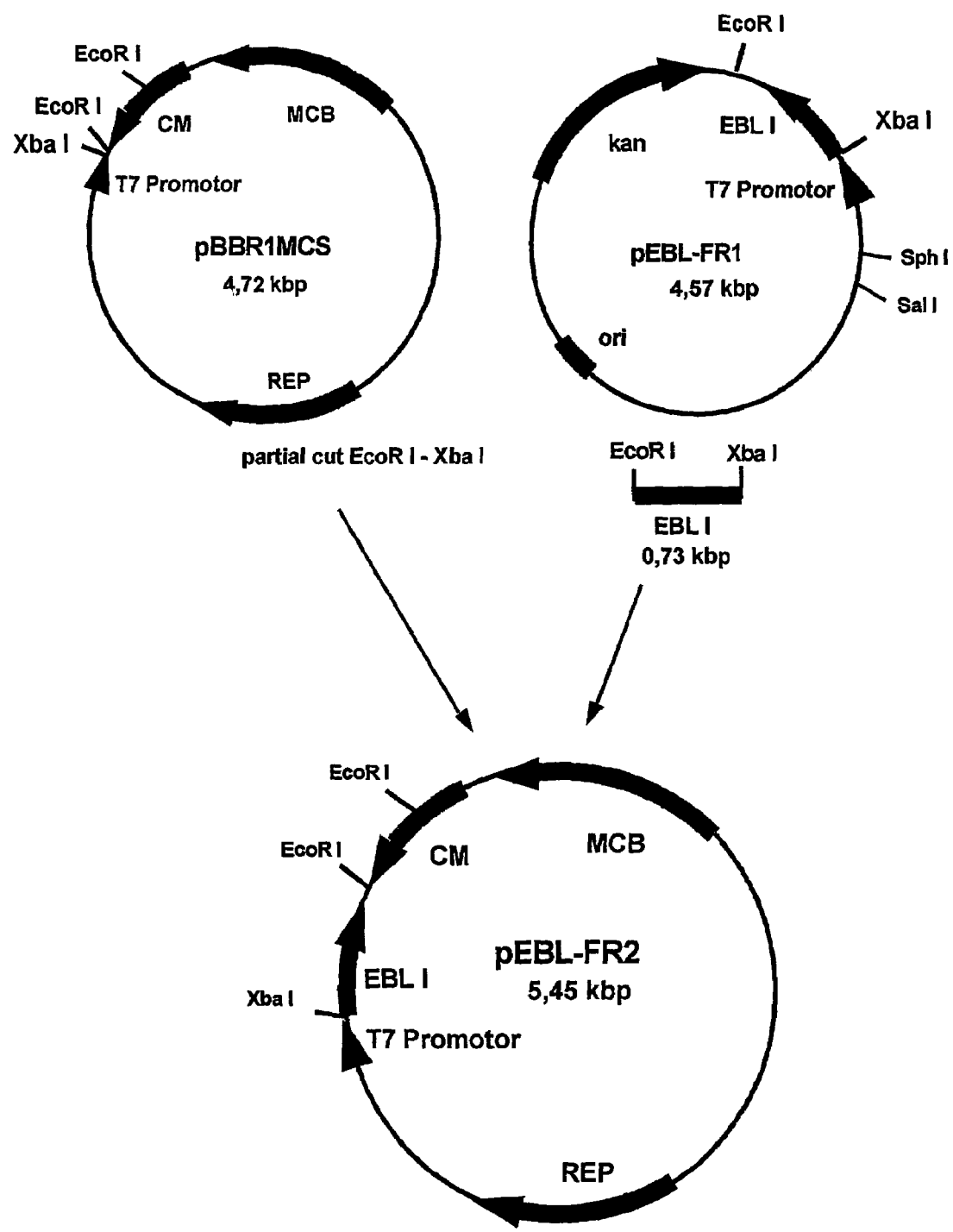

The XbaI-BamHI EBLI fragment was ligated into the XbaI and BamHI sites of the vector pET9a (6). The ligation was transformed in the *E. coli* strain K12 XL10. Transformants were selected on LB plates containing 30 µg/ml kanamycine. After DNA isolation and restriction analysis positive plasmids were sequenced. The plasmid with the correct DNA sequence was named pEBL-FR1 (FIGS. 1, 2).

3. Transformation of the EBLI Construct in the *E. coli* Strain BL21(DE3)

For expression of the EBLI peptide the plasmid pEBL-FR1 was transformed in the *E. coli* strain BL21(DE3) (Fa. Novagen, 6).

Transformands were selected on LB media containing 30 µg/ml kanamycine und 1% glucose. After DNA isolation from growing transformants the plasmids were analyzed by restriction analysis with XbaI and BamHI (data not shown).

4. Expression of the EBLI Peptide

For the expression of EBLI we used the described *E. coli* strain BL21(DE3)+pEBL-FR1.

In this strain the T7 polymerase gene is under control of the lac UV5 promoter and this construct is integrated in the genome (6). Under non induced conditions the lac UV5 promoter is blocked by the laci repressor. Under induced conditions IPTG inactivates the lac repressor protein and the T7 polymerase is expressed. T7 polymerase binds to the T7 promoter region of the plasmid pEBL-FR1 and induces the expression of EBLI.

The expression of the EBLI peptide was induced by adding IPTG to an endconcentration of 0.4 mM at a optical density ($OD_{600nm}$) of 0.5 of the culture. After 2,5 hours additional incubation at 32° C. the cells were prepared described in Materials and Methods. A non induced culture serves as control.

5. Localisation and Purification of the EBLI Peptide

From our construction strategy we suspected that EBLI is located at the cell membrane in the periplasmic space. Since the EBLI peptide is highly charged we decided to extract the membrane fraction with $H_2O$ to isolate a enriched fraction of the peptide.

To control the expression and localisation of the EBLI peptide the following fractions were isolated and analyzed on a 17% Laemmli SDS page gel (data not shown).

Results:

Under induction conditions a protein band with a molecular mass of approximately 16 kDa was detected. This signal was also detectable in the membrane fraction of induced cells. Moreover it was extractable with $H_2O$ from the membrane fraction. With micron columns it was possible to concentrate this protein. In the medium (TCA precipitation) the protein was not detectable.

The theoretical molecular mass of the intact protamine is about 6 kDa. The difference to the induced peptide could be explained by the strong positive charge of the protamine peptide; strong positive charged proteins (protamine, histones) does not migrate like their molecular mass would be expected.

We see this different migration effect also with commercial available protamine, which we used as a control. In the course of isolating EBL I and in order to be able to localize quickly the target location of the overexpressed EBL I, we decided to raise an antibody against commercial protamine from Sigma. As a protein chemist, normally we estimate the homogeneity of the antigen (protamine) before using it to raise the antibody. Surprisingly, amino acid sequence analysis revealed many N-terminal amino acids at each step, indicating inhomogenity. By a combination of mass spectroscopy, HPLC and amino acid sequence analysis, we came to the definite conclusion that the preparation purchased from Sigma was composed of at least ten different fragments of protamine. Unfortunately, we could not identify the presence of any intact protamine consisting of at least 32 amino acids, indicating that the intact molecule is not present, although our method is extremely sensitive. In this situation we were not able to use the commercially available protamine as antigen for raising antibodies, especially since if this had been homogeneous the higher molecular size of poly-protamine would have given a better antigenic response.

Thus, mass spectroskopy analysis has revealed that this protamine fraction consists of a mixture of 10-15 amino acids long peptides with a molecular mass of about 2 kDa. In the SDS page this fraction migrates at a molecular mass of about 10 kDa.

For the verification that we have expressed the intact protamine, the induced peptide was analysed by mass spectroskopy.

Expression of EBLI in *Pseudomonas fluorescens*

Our aim was the expression of the peptide EBLI in *Pseudomonas fluorescens* with a special phenotype who tolerate protamine concentrations of more than 40 mg/ml in respect to *Escherichia coli* which does not grow at concentration of 1,5 mg/ml.

For expression of the peptide EBLI in *Pseudomonas fluorescens* we used a system with two plasmids.

The first plasmid (pML5T7) contains the T7 polymerase under the control of the lacUV5 promoter, the lacIq gene and the gene for tetracyclin resistence. The expression of the T7 polymerase is inducible after adding of IPTG (endconcentration of 2 mM, 9).

In the second plasmid the structure gene of EBLI is cloned downstream of the T7 promoter.

Therefore we have constructed two plasmids (cf. FIGS. 1, 2):
1. pEBL-FR2: The synthesized EBLI construct inclusive the T7 termination signals was cloned under the control of the T7 promoter of the plasmid pBBR1MCS.
2. pEBL-FR4: The plasmid pEBL-FR1 was not replicated in *Pseudomonas fluorescens*. Therefore we fused the plasmid with the replicon pRO1600 from *Pseudomonas aeruginosa*.

Construction of the Plasmid pEBL-FR2 (FIG. 2)

The vector pBBR1MCS was partially cut with EcoRI and XbaI and then ligated with the fragment EcoRI-XbaI (0.74 kB) isolated from the plasmid pEBL-FR1. This EcoRI-XbaI fragment contains the synthesized EBLI construct and the T7 termination signals.

The vector pBBR1MCS was partially cut with EcoRI and XbaI and then ligated with the fragment EcoRI-XbaI (0.74 kB) isolated from the plasmid pEBL-FR1.

From growing transformants the plasmid was isolated and restricted with XbaI and EcoRI. The resulting fragment has a size of 0.74 kB and was not distinguishable from an other fragment resulting from the second EcoRI site of the vector. Therefore we restricted the plasmid with XbaI and NcoI resulting in sigals of 0.5 kB for the vector and 1,23 kb for the correct construct.

Transformation of the Strain wis 437 from *Pseudomonas fluorescens*

In a first transformation the strain 437 was transformed by electroporation with the plasmid pML5T7 (11). For the selection of transformants the cells were plated on LB plates with a tetracyclin concentration of 10 µg/ml. After DNA isolation the plasmid was analyzed by restrictions analysis.

In a second transformation the strain wis 437+pML5T7 was transformed by electroporation with the plasmid pEBL- FR2 and with the vector pBBR1MCS. For the selection of transformants the cells were plated on LB plates with a end-concentration of 10 µg/ml tetracycline, 340 µg/ml chloramphenicol and 1% glucose. From growing transformants plasmids were isolated and controlled by a restriction analysis (data not shown).

Expression of EBLI in *Pseudomonas fluorescens*

The expression of the EBLI peptide was induced by adding IPTG to an endconcentration of 2 mM at a optical density ($OD_{600nm}$) of 0.5 of the culture. After 2,5, 5 and 7,5 hours additional incubation at 32° C. the cells were broken with glass beads as described in Materials and Methods. A non induced culture serves as an control. To reduce the stress for the growing cells (the media contain tetracycline and kanamycine and the cells express EBLI) we have decreased the antibiotica concentration for tetracycline to 5 µg/ml and, for kanamycine to 10 µg/ml. The grow curve showed that under low antibiotic conditions the cells have a slight growth advantage without loss of plasmids (Data not shown).

Induction of the EBLI Peptide in *P. fluorescens* with IPTG

The cultures were splitted. To one culture IPTG was added to induce the expression of the EBLI peptide. The other culture served as an uninduced control. After additional incubation of 2,5, 5 and 7,5 hours at 32° C. the cells were harvested, broken with glass beads and the total cell protein was isolated (see materials and methods). The proteins were analyzed on a 17% Laemmly SDS page gel (data not shown).

Results:

Under induction conditions an expressed peptide band with a molecular mass of approximately 16 kDa was detected. After 7,5 hours additional incubation under induction conditions the highest concentration of the induced protein was yielded. Under low antibiotic concentrations the gel showed a slightly more expression of the peptide caused by the better growth of the cells.

Construction of the Plasmids pEBL-FR4 (FIG. 1)

The plasmid pEB1 (10) was restricted with the restriction enzyme PstI and the resulting fragment (replikcon pRO1600: 1,8 kB) was cloned in the vector pUC19 (restricted with Pst). After plasmid isolation from growing transformants the pRO1600 fragment was isolated with the restriction enzymes PaeI and SalI. This fragment was cloned in the plasmid pEBL-FR1 (restricted with PaeI (SphI) and SalI) (see FIG. 1).

Materials and Methods

1. Organisms and Plasmids

For the experiments certain *Pseudomonas fluorescens* and *Pseudomonas aeruginosa* strains were used as well as different *Escherichia coli* strains. Table 1 shows the utilized strains and their characteristics.

TABLE 1

*Pseudomonas* and *Escherichia coli* strains

| Strain | Relevant genotypes |
|---|---|
| *E. coli* | |
| K12 XL10 | $Tet^R\Delta(mcrA)$ 183 Δ(mcrCB-hsdSMR-mrr) 173 endA1 supE44 thi-1 recA1 gyrA96 relA1 lac Hte[F' proAB lacI$^q$ZΔM15 Tn10 (Tet$^R$) Amy Cam$^R$] |
| BL21(DE3) | F$^-$ ompT hsdS$_B$(r$_B^-$ m$_B^-$) gal dcm (DE3) |
| DH5 alpha | supE44 ΔlacU169 (φ80lacZ ΔM15) hsdR17 recA1 endA1 gyrA96 thi-1 relA1 |

TABLE 1-continued

*Pseudomonas* and *Escherichia coli* strains

| Strain | Relevant genotypes |
|---|---|
| *Pseudomonas fluorescens* | |
| wis 437 (DSM50106) | wild type |
| wis 437 + pML5T7 | pML5T7 |
| wis 437 + pML5T7 + pEBL-FR2 | pEBL-FR2 |

TABLE 2

Plasmids

| Plasmid | Relevant genotypes[a] | host strain |
|---|---|---|
| pET9a | km$^r$, T7 promoter upstream of the cloning sites BamHI and XbaI | *E. coli* BL21(DE3) |
| pBBR1MCS | cm$^r$, T7 promoter upstream of a polycloning site | *E. coli* DH5 alpha |
| pEB1 | tet$^r$, the T7 polymerase under control of the lacUV5 promoter, lacIq gene, origin of replication (pRO1600) from *Pseudomonas aeruginosa* | *E. coli* DH5 alpha |
| pML5T7 | tet$^r$, the T7 polymerase under control of the lacUV5 promoter and the lacIq gene | *E. coli* DH5 alpha |
| pUC19 | amp$^r$, polycloning site | *E. coli* DH5 alpha |
| pEBL-FR1 | synthesized sequence of EBLI | *E. coli* BL21 (DE3) |
| pEBL-FR2 | synthesized sequence of EBLI | *E. coli* DH5 alpha |
| pEBL-FR4 | synthesized sequence of EBLI | *E. coli* DH5 alpha |
| pEBL-FR3 | replicon pRO1600 from *Pseudomonas aeruginosa* | *E. coli* DH5 alpha |

[a]km: kanamycin, cm: chloramphenicol, tet: tetracyclin, amp: ampicilline, $^r$resistent Chemicals and Enzymes Used

| Product | Source |
|---|---|
| 40% acrylamide-bisacrylamide soluton (29:1) (Rotiphorese ®) | Fa Roth (Karlsruhe, Germany) |
| agar and media | Fluka Chemie GmbH (Buchs, Germany) |
| Agarose, Seakem LE | FMC Bioproducts Rockland, Maine USA |
| Ammoniumperoxodisulfate (APS) | Fa Roth (Karlsruhe, Germany) |
| Ampicilline (Amp) | Sigma Aldrich (Taufkirchen, Germany) |
| Boric acid | Fa Roth (Karlsruhe, Germany) |
| Bromphenol blue | Sigma Aldrich (Taufkirchen, Germany) |
| Chloramphenicole (Camp) | Fa Roth (Karlsruhe, Germany) |
| Coomassie brillant blue R250 | Fa Roth (Karlsruhe, Germany) |
| DNA Isolation kits | Fa Qiagen, (Hilden, Germany) |
| Dithiothreitol (DTT) | Fa Roth (Karlsruhe, Germany) |
| Ethanol | Fa Roth (Karlsruhe, Germany) |
| Ethylenediamine tetraacetic acid (EDTA) | Fa Roth (Karlsruhe, Germany) |
| Glacial acetic acid | Fa Roth (Karlsruhe, Germany) |
| Glycerol | Fa Roth (Karlsruhe, Germany) |

-continued

| Product | Source |
| --- | --- |
| Glycine | Fa Roth (Karlsruhe, Germany) |
| IPTG | Fa Roth (Karlsruhe, Germany) |
| Kanamycine (Kan) | Sigma Aldrich (Taufkirchen, Germany) |
| Methanol | Fa Roth (Karlsruhe, Germany) |
| Potassium dihydrogen phosphate | Fa Roth (Karlsruhe, Germany) |
| Potassium chloride | Fa Roth (Karlsruhe, Germany) |
| Protamine from salmon | Sigma Aldrich (Taufkirchen, Germany) |
| Protein marker (low range) | Sigma Aldrich (Taufkirchen, Germany) |
| Restrictions enzymes, T4 ligase, DNA marker | MBI Fermentas (St. Leon-Rot, Germany) |
| Sodium chloride | Merck (Darmstadt, Germany) |
| Sodium dihydrogen phosphate monohygrate | Merck (Darmstadt, Germany) |
| Sodium dodecyl sulfate (SDS) | Fa Roth (Karlsruhe, Germany) |
| Tetracycline (Tet) | Sigma Aldrich (Taufkirchen, Germany) |
| N,N,N',N'-Tetramethylethylendiamine (TEMED) | Fa Roth (Karlsruhe, Germany) |
| Tris base | Fa Roth (Karlsruhe, Germany) |
| Xylene xyanol | Fa Roth (Karlsruhe, Germany) |

Media: All strains were grown on rich medium (Luria-Bertani (LB)) containing 1% glucose at 32° C. LB media and plates were purchased from Fa. Fluka Chemie GmbH (Buchs, Germany):

| LB media: | |
| --- | --- |
| Tryptone | 10 g/l |
| Yeast extract | 5 g/l |
| Sodium chloride | 5 g/l |

Dissolve 20 g in 1 litre destined water and adjust the pH to 7,2. Sterilize by autoclaving at 121° C. for 15 min.

| LB agar: | |
| --- | --- |
| Tryptone | 10 g/l |
| Yeast extract | 5 g/l |
| Sodium chloride | 5 g/l |
| Agar | 10 g/l |

Dissolve 30 g in 1 litre destilled water and adjust the pH to 7,2. Sterilize by autoclaving at 121° C. for 15 min.

For selection of transformed *E. coli* we used the following antibiotic concentrations:
Tetracycline 10 µg/ml
Kanamycine 10 µg/ml
Chloramphenicol: 25 µg/ml
Ampicilline: 40 µg/ml For selection of transformed *Pseudomonas fluorescens* we used the following antibiotic concentrations:
Tetracycline 10 µg/ml
Kanamycine 30 µg/ml
Chloramphenicol: 340 µg/ml Buffers
TBE Puffer: per 1 litre
5,4 g Tris base
2,75 g boric acid
20 ml 0.5M EDTA pH8,0

5× agarose gel loading buffer:
0.25% bromphenol blue
0.25% xylene cyanol FF
30% glycerol
Phosphat-buffered Saline (PBS)
8 g NaCl
0.2 g KCl
1,44 g $Na_2HPO_4$
0.24 g $KH_2PO_4$
adjust pH to 7,4 with HCl and autoclave for 20 min at 121° C.

Plasmid Constructions:

All plasmids were constructed in *E. coli* DH5 alpha by standard protocols

Protocol for competent cells of *E. coli*
1. Pick a single colony (2-3 mm in diameter) and inoculate a 5 ml culture of LB broth. Incubate the culture overnight with at 37° C. with vigorous shaking.
2. Inoculate 100 ml LB broth with 1 ml of the over night culture and incubate at 37° C.
3. When a optical density (a $OD_{600}$) of 0.3-0.4 is reached the cells were transferred in sterile centrifugation tubes and stored for 10 min on ice
4. Recover the cells by centrifugation at 4000 rpm for 10 min at 4° C. in a Sorvall SS34 rotor.
5. Decant the media from the cell pellets. Stand the tubes in an inverted position for 1 min to allow the last traces of media to drain away.
6. Resuspend each pellet in 50 ml of ice-cold 0.1 M $CaCl_2$ and store on ice for 20 min.
7. Recover the cells by centrifugation at 4000 rpm for 10 min at 4° C. in a Sorvall SS34 rotor.
8. Decant the fluid from the cell pellets and stand the tubes in an inverted position for 1 min to allow the last traces of fluid to drain away.
9. The pellet was resuspended in 9 ml of ice-cold 0.1 M $CaCl_2$.
10. Ice cold glycerol was added to the cell suspension to a end concentration of 15%
11. The cell suspension was portionated (500 µl in sterile microfuge tubes) and stored at −80° C.

Transformation of Competent Cells
1. To 200 µl competent cells 20 µl of the ligation mixture (not more than 200 ng DNA) was added and the tube stored on ice for 40 min.
2. heat shock at 42° C. for 2 min
3. Rapidly transfer the tubes to an ice bath. Allow the cells to chill for 1-2 min.
4. 1 ml of LB medium was added and the cells than incubated for 1 hour at 37° C.
5. The cells were harvested in a microfuge (4000 rpm for 5 min) and spread on a agar plate supplemented with the appropriate antibiotics.
6. Colonies should appear in 12-16 hours.

Mini Preparation of Plasmid DNA
1. Resuspend pelleted bacterial cells in 250 µl Buffer P1 and transfer to a microcentrifuge tube.
2. Add 250 µl Buffer P2 and gently invert the tube 4-6 times to mix.
3. Add 350 µl Buffer N3 and invert the tube immediately but gently 4-6 times.
4. Centrifuge for 10 min at maximum speed in a tabletop microcentrifuge.
5. Apply the supernatants form step 4 to the QIAprep column by decanting or pipetting.
6. Centrifuge for 30-60 s. Discard the flowthrough.

7. Wash the QIAprep spin column by adding 0.5 ml Buffer PB and centrifuging for 30-60 s. Discard the flowthrough.
8. Wash QIAprep spin column by adding 0.75 ml Buffer PE and centrifuging for 30-60 s.
9. Discard the flowthrough and centrifuge for an additional 1 min to remove residual wash buffer.
10. Place the QIAprep column in a clean 1.5 ml microcentrifuge tube. To elute DNA, add 50 µl Buffer EB (10 mM Tris-Cl, pH 8.5) to enter the center of each QIAprep column, let stand for 1 min and centrifuge for 1 min.
11. For a restriction analysis we used 3 µl for high copy plasmids and 8 µl for low copy plasmids Midi Preparation of Plasmid DNA 1. Pick a single colony from a freshly selective plate and inoculate a starter culture of 2-5 ml LB medium containing the appropriate selective antibiotic. Incubate for ~8 h at 37° C. with vigorous shaking (~300 rpm).
2. Dilute the starter culture 1/500 to 1/1000 into selective LB medium. For high-copy plasmids inoculate 25 ml medium. For low-copy plasmids, inoculate 100 ml medium. Grow at 37° C. for 2-16 h with vigorous shaking (~300 rpm).
3. Harvest the bacterial cells by centrifugation at 4000 rpm for 15 min at 4° C. in a Sorvall SS34 Rotor.
4. Resuspend the bacterial pellet in 4 ml of Buffer P1.
5. Add 4 ml of Buffer P2, mix gently but thoroughly by inverting 4-6 times, and incubate at room temperature for 5 min.
6. Add 4 ml of chilled Buffer P3, mix immediately but gently by inverting 4-6 times and incubate on ice for 15 min.
7. Centrifuge at 8000 rpm for 30 min at 4° C. in a Sorvall SS34 Rotor. Remove supernatant containing plasmid DNA promptly.
8. Equilibrate a QUIAGEN-tip 100 by applying 4 ml Buffer QBT and allow the column to empty by gravity flow.
9. Apply the supernatant from step 7 to the QUIAGEN-tip and allow it to enter the resin by gravity flow.
10. Wash the QUIAGEN-tip with 2×10 ml Buffer QC.
11. Elute DNA with 5 ml Buffer QF.
12. Precipitate DNA by adding 3.5 ml room temperature isopropanol to the eluted DNA. Mix and centrifuge immediately at 8000 rpm for 30 min at 4° C. in a Sorvall SS34 Rotor. Carefully decant the supernatant.
13. Wash DNA pellet with 2 ml of room-temperature 70% ethanol and centrifuge at 8000 rpm for 10 min in a Sorvall SS34 rotor. Carefully decant the supernatant without disturbing the pellet.
14. Air-dry the pellet for 5-10 min and redissolve the DNA in a suitable volume of $H_2O$ Restriction Analysis, DNA Ligations Enzymatic reactions were performed according the manuals of MBI Fermentas.

Standard restriction analysis were performed in volume of 20 µl with 5 Unit of the appropriate enzyme.

Standard Agarose Gels: 0.7%, 40 ml 0.28 g agarose were dissolved in 40 ml TBE buffer. The agarose solution was melted in a micro wave until the solution is clear. After cooling to 50° C. 4 µl of a 1% Ethidium bromid solution was added.

After the gel is completely set the samples of DNA were mixed with 5× gel loading buffer and load into the slots. The gel was running at 100 Volt in a gel chamber from Stratagene.

DNA Fragment Isolation from Agarose Gels

1. Excise the DNA band from the agarose gel with a clean, sharp scalpel.
2. Weigh the gel slice. Add 3 volumes of Buffer QX1 to 1 volume of gel for DNA fragments of 100 bp to 4 kb.
3. Resuspend QIAEX II by vortexing for 30 sec.
4. Add QIAEX II according to the table below and mix. Incubate at 50° C. for 10 min. Mix every 2 min to keep QIAEX II in suspension.
5. Centrifuge the sample for 30 sec and carefully remove supernatant with a pipet.
6. Wash the pellet with 500 µl of Buffer QX1.
7. Wash the pellet twice with 500 µl of Buffer PE.
8. Air-dry the pellet for 10-15 min or until the pellet becomes white.
9. To elute DNA, add 20 ml of 10 mM Tris-HCl, pH 8.5 or $H_2O$ and resuspend the pellet by vortexing. Incubate at room temp. for 5 min.
10. Centrifuge for 30 sec. Carefully pipet the supernatant into a clean tube.
11. Optional: repeat steps 9 and 10 and combine the eluates.

Electroporation von *Pseudomonas fluorescens*

The electroporation conditions are described by Bloemberg et. al. (11)

Prepare an 2 ml sample of an overnight culture of cells in LB media and inoculate into 50ml of fresh LB incubate at 32° C. with shaking until the late log phase When an optical density ($OD_{600nm}$) of 0.5-1,0 is reached ($10^{10}$Cell/ml) chill the culture for 30min on ice centrifuge the culture at 4° C. in a SS34 rotor for 10 min at 4000 rpm wash the cell with 25 ml ice-cold 10% glycerol wash the cells with 1 ml ice-cold 10% glycerol resuspend the cells in 200 µl ice-cold 10% glycerol load a pre chilled 2-mm-gap electroporation cuvette with 50 µl of the cellsuspension add 1-3 µl DNA (0.5 µg DNA)

electroporation was performed a 1,8 kV with an *E. coli* Pulser (Bio-Rad, Melville, N.Y.)

after the pulse resuspend the cells in 1 ml LB media and incubate for 1 hour at 32° C.

After electroporation the cells were incubated for one hour at 32° C., centrifuged for 5 min at 4000 rpm and than plated on LB agar with 1% glucose, supplemented with the appropriate antibiotics:

Expression and Purification of the EBLI Peptid in *E. coli* Strain BL21 (DE3)

1. Expression of the EBLI Peptid

The expression of the target gene followed the protocols of Fa Novagen (6).

Inoculate a 5 ml LB culture containing 30 µg/ml kanamycin and 1% glucose. Incubation at 32° C. over night under vigorous shaking.

Inoculate a 100 ml LB Medium culture containing 30 µg/ml Kanamycin, 1% Glukose with 1 ml of the over night culture.

Inkubation at 32° C. under under vigorous shaking until a optical density ($OD_{600nm}$) of 0.5 is reached split the culture into 2×50 ml cultures:
A: uninduced control
B: IPTG was added to a final concentration of 0.4 mM (induced culture)

The incubation was continued for 2,5 hours

The cells were harvested by centrifugation at 4000 rpm for 10 min at 4° C. in a Sorvall SS34 rotor.

Traces of media from the pellet were removed with a pipette. The pellet was than suspended in 500 µl phosphate buffered saline (PBS) and stored at −20° C.

The supernatant was stored in −20° C.

2. Preparation of the Medium

The trichloroacetic acid (TCA) preparation followed the protocol of Fa Novagen (6)

100 µl (1/10 volume) of 100% TCA to 1 ml of medium was added and vortex for 15 sec.

Incubation on ice for a minimum of 15 min.

The suspension was centrifuged at 12000 rpm for 10 min at 4° C. in a Sorvall SS34 rotor.

The pellet was washed with 1 ml acetone and centrifuged at 12000 rpm for 5 min at 4° C. in a Sorvall SS34 rotor This step was repeated.

The pellet was air dried for about 60 min and than resuspended in 100 µl PBS.

100 µl 2× SDS gel loading buffer was added

For denaturation of the proteins the probe was heated for 3 min at 90° C. and stored at −20° C.

3. Disruption of the Cells

The cells were mechanically disrupted by vortexing with glassbeads (25 µm).

The cell suspension (in 500 µl PBS) was transferred in a reaction tube. Glass beads were added until the lower meniscus of the suspension is reached.

The suspension was vortexed for 20 sec and than stored on ice for 20 sec. This step was 12× repeated (whole vortexing time of 4 min).

The glass beads were washed with 500 µl of PBS. This step was repeated until the endvolume of the wash fraction was 1 ml.

To 20 µl of this suspension 20 µl 2× SDS gel loading buffer was added

For denaturation of the proteins the probe was heated for 3 min at 90° C. and stored at −20° C.

4. Preparation of the Cellwall-membranefraction.

To isolate the cellwall-membranefraction the disrupted cells were centrifuged at 12000 rpm for 10 min at 4° C. in a Sorvall SS34 Rotor supernatant: cytoplasmic fraction (about 800 µl): To 20 µl of the fraction 20 µl 2× SDS gel loading buffer was added, heated 3 min at 90° C. and then stored at −20° C.

pellet: cellwall-membrane fraction (suspended in 100 µl PBS): To 12,5 µl of the fraction 12,5 µl 1 2× SDS gel loading buffer was added, heated 3 min at 90° C. and then stored at −20° C.

5. Isolation of the Peptide EBLI from the Water Soluble Fraction of the Cellwall-membrane Fraction The pellet (cellwall-membrane fraction) was extracted with 500 µl $H_2O$ and centrifuged at 12000 rpm for 5 min at 4° C. in a Sorvall SS34 Rotor.

For quantitative extraction this step was repeated for three times and the supernatants were combined.

pellet: water insoluble membranefraction (suspended in 100 µl PBS): To 10 µl of the fraction 10 µl 2× SDS gel loading buffer was added, heated 3 min at 90° C. and then stored at −20° C.

supernatant: water soluble membrane fraction (about 1400 µl): To 25 µl of the fraction 25 µl 2× SDS gel loading buffer was added, heated 3 min at 90° C. and then stored at −20° C.

6. Concentration of the Water Soluble Membrane Fraction

1400 µl were concentrated on a Micron YM-3 column to an end volume of 160 µl. To 20 µl of the fraction 20 µl 2× SDS gel loading buffer was added, heated 3 min at 90° C. and then stored at −20° C.

Concentrating of Protein Solutions

To concentrate the water soluble membrane fraction we use the Microcon Centrifugal Filter Devices YM-3 ( Millipore, Bedford, USA ).

1. Insert Microcon sample reservoir into vial
2. Pipette solution into sample reservoir (0.5 ml maximum volume), without touching the membrane with the pipette tip. Seal with attached cap.
3. place the tube in a centrifuge for 1,5 ml tubes
4. centrifuge at 13000 g for 30 min (400 µl are spin through the columm)
5. if nescessary add additional 400 µl on the column and repeat the centrifugation.
6. remove assembly from centrifuge. Seperate vial from the sample reservoir.
7. Place sample reservoir upside down in a new vial, then spin 3 minutes at 1000×g to transfer concentrate to vial.
8. Remove from centrifuge. Seperate sample reservoir. Store the concentrate at −20° C.

Literature:

1. Hirsch, J. G. (1958) Bacteriacidal action of histone. *J. Exp. Med.* 107: 925-944
2. Islam, N. M., Itakura, T., Motohiro, T. (1984) Antibacterial spectra and minimum inhibitory concentration of clupeine and salmine. *Bull. ipn. Soc. Sci. Fish* 50: 1705-1708
3. Johansen, C., Gill, T., Gram, L. (1995) Antibacterial effect of protamine assayed by impedimetry. *J. Appl. Bacteriol.* 78: 297-303
4. Ando, T., Watanabe, S. (1969) A new method for fractionation of protamines and the amino acid sequences of samline and three components of iridine. *Int. J. Protein Res.* 1: 221-224
5. Wickner, W., Driessen, A. J. M., Hartl, F.-U. (1991) *Annu. Rev. Biochem.* 60 101-124
6. Produktbeschreibung der Fa Novagen. (1994) The pET System: Your choice for expression. *inNovations* 1: 1. 1-58
7. Sambrook, J., Fritsch, E. F., Maniatis, T. (1989) Molecular cloning: a laboratory manual, 2nd ed. *Cold Spring Harbor Laboratory Press,* Cold Spring Harbor, N. Y.
8; Laemmli U. K. (1970) Cleavage of structural proteins during the assembly of the head of bacteriophage T4. *Nature* 227 680-685
9. Rosenau, F., Liebeton, K., Jaeger, K.-E. (1998) Überexpression extrazellularer Enzyme in *Pseudomonas aeruginosa Biospektrum* 4: 38-41
10. Brunschwig, E., Darzins, A., (1992) A two-component T7 system for the overexpression of the genes in *Pseudomonas aeruginosa. Gene* 111: 35-41
11. Bloemberg, G. V., O'Toole, G. A., Lugtenberg, B. J. J., Kolter, R. (1997) Green fluorescent protein as a marker for *Pseudomonas* spp. *Appl. and Envir. Microbiol.* 63: 11, 4543-4551
12. Kovach, M. E., Phillips, R. W., Elzer, P. H., RoopII, R, M., Peterson, K. M. (1994) pBBR1MCS: A broad-host-range cloning vector *BioTechniques* 16: 5, 801-802
13. Hanahan, D. (1983) Studies on transformation of *Escherichia coli* with plasmids. *J. Mol. Biol.* 166: 557-580
14. DSMZ-Deutsche Stammsammlung von Mikroorganismen und Zellkulturen GmbH, Braunschweig, Germany
15. Yanisch-Perron, C., Vieira, J. and Messing, J. (1985) *Gene* 33, 103-119

EXAMPLES (SECTION II)

Bacterial Growth Conditions

Bacteria are cultured in Luria-Bertani broth (LB, WWW 2001) respectively tryptic soy broth (TSB, DIN EN 1040, 1997) at 37° C. All bacterial strains are maintained as frozen stocks at −80° C. in TSB, Luria-Bertani broth.

Throughout the experiments strains are subcultured every 2 weeks on TSA (tryptic soy agar; 15 g l$^{-1}$ agar) or LBA (Luria-Bertani agar; 15 g l$^{-1}$ agar) depending upon the type of bacteria and experiment and kept at 4° C. The incubation temperature is 37° C. except for photo-heterotrophic bacteria (30° C.). Before experimental use, cultures are propagated twice in the corresponding broth (pH 7.2±0.2) for 18-24 h.

Parameters Applied to Determine the Inhibitory Effect of Protamine

The growth curve is determined by measuring the optical density (OD), growth rate and doubling time. Additionally, the number of colony forming units is determined by counting bacterial spots.

Bacterial growth is monitored by recording the increase in optical density (OD) at 560 nm in a spectrophotometer (Ultrospec 1000, Pharmacia Biotech, England). Sterile medium is used as reference. Growth rate (μ) and doubling time ($t_d$) are calculated during the logarithmic growth phase according to SCHLEGEL (1992). At given times, 100 μl aliquots of the samples are removed and spread on corresponding agar plates. If necessary, the samples are diluted by factors between $10^2-10^8$ to ensure good count ability. Colony forming unit determination (CFU/ml) is carried out in duplicate using a CCD camera module (Sony Corp., Japan) applying the BioProfil Software V 2000.01 (Vilber Lourmat, France).

Use of the Basic Bactericidal Activity Test Method DIN EN 1040 (DEV-1997)

Basic bactericidal activity is determined according to the European standard method DIN EN 1040 (DEV, 1997). Bacterial cells are cultured on tryptone soy agar plates (tryptone-soy-agar, TSA, tryptone: 15.0 g*l$^{-1}$; soy-peptone: 5 g*l$^{-1}$; NaCl: 5 g*l$^{1}$; agar: 15 g*l$^{-1}$). Bacterial suspensions of $1.5*10^8-5.0*10^8$ bacteria per milliliter are subjected to several concentrations of Protamine. After an incubation time of 60 minutes, two 100 μl aliquots of the samples are filtered separately through presterilized cellulosic membrane filters (Osmonics, Minnetonka, USA, diameter 47 mm; pore size 0.45 μm; Catalog No. E04WG047S1). The filters are firmly placed onto TSA-plates and incubated at 37° C. for 24-48 hours. The number of colony forming units is determined by counting bacterial spots.

Reagents

A commercially available protamine from Salmon is obtained from Sigma Aldrich (Taufkirchen, Germany). A stock solution is prepared by dissolving protamine in distilled water. The solution is then sterilized with Rotabilo© filter units (0.22 μm; Carl Roth, Karlsruhe, Germany) and stored at −20° C. until use.

Determination of Bactericidal Effect of Biological Buffers With or Without Protamine on Gram-negative Bacteria In all experiments the starting inoculum is $10^7$ cells. The data shown are average means of three replicates.

TABLE 3

Effect of biological buffers with or without different concentrations of Protamine on the growth of *Escherichia coli* DH5α

|  | control | 0.1M NaHCO$_3$ | 0.4M citrate | 0.1M NaHCO$_3$ + 0.4M citrate | | | | |
| --- | --- | --- | --- | --- | --- | --- | --- | --- |
| μ [h$^{-1}$] | 0.468 | 0.230 | 0.185 | 0 | | | | |
| $t_d$ [h] | 1.48 | 3.01 | 3.75 | 0 | | | | |
| 0.1M NaHCO$_3$ + 0.4M citrate Protamine [mg/ml] | 0.005 | 0.01 | 0.02 | 0.04 | 0.08 | | | |
| μ [h$^{-1}$] | 0 | 0 | 0 | 0 | 0 | | | |
| $t_d$ [h] | 0 | 0 | 0 | 0 | 0 | | | |

Figure 3:
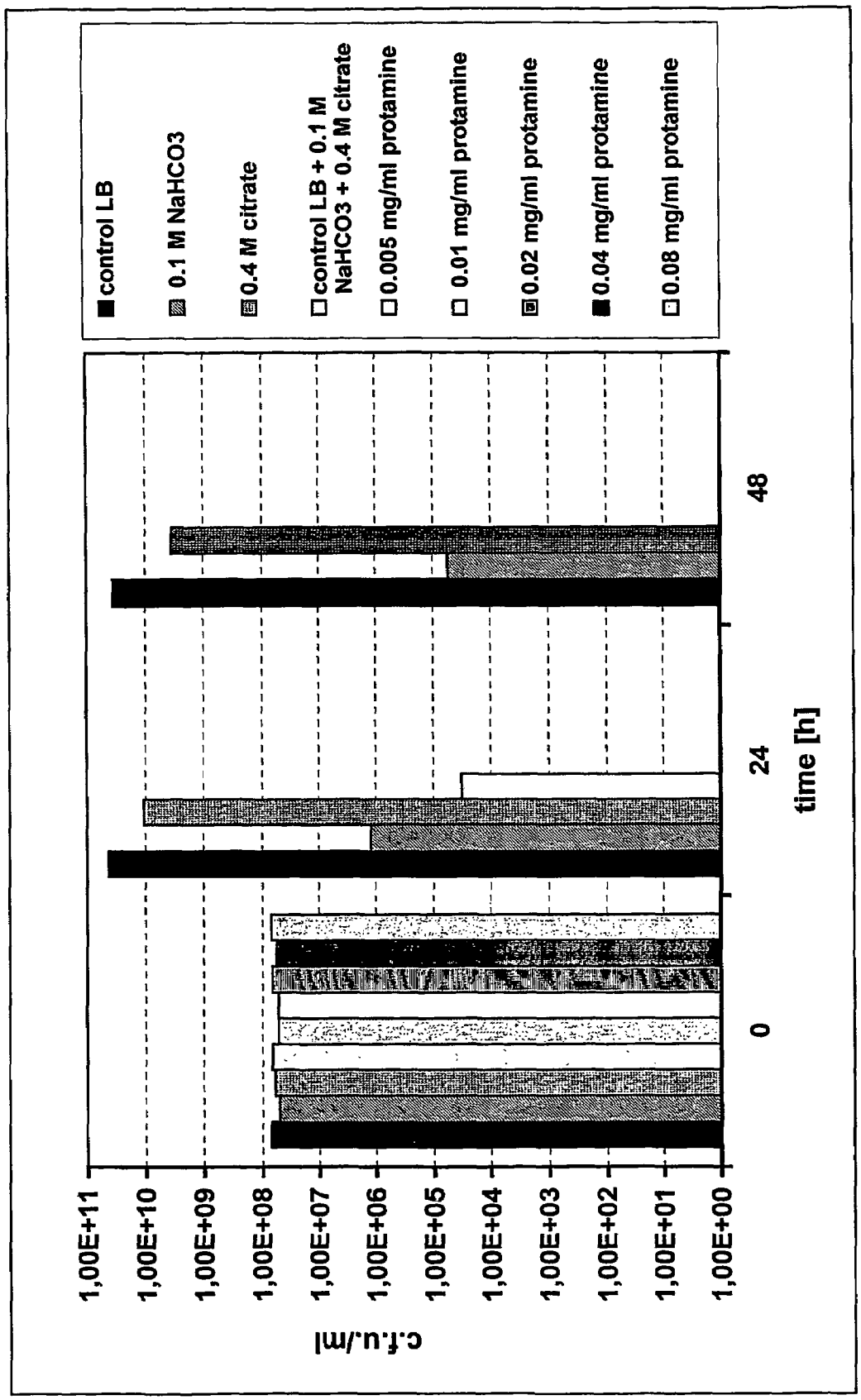

The results are shown in FIG. 3.

Determination of Bactericidal Effect of Biological Buffers With or Without Protamine on Gram-positive Bacteria In all experiments the starting inoculum is $10^7$ cells. The data shown are average means of three replicates.

TABLE 4

Effect of biological buffers with or without different concentrations of Protamine on the growth of *Micrococcus luteus* DSM 348

|  | control | 0.1M NaHCO$_3$ | 0.4M citrate | 0.1M NaHCO$_3$ + 0.4M citrate | | | | | |
| --- | --- | --- | --- | --- | --- | --- | --- | --- | --- |
| μ [h$^{-1}$] | 0.389 | 0 | 0 | 0 | | | | | |
| $t_d$ [h] | 1.78 | 0 | 0 | 0 | | | | | |
| 0.1M NaHCO$_3$ + 0.4M citrate protamine [mg/ml] | 0.005 | 0.01 | 0.02 | 0.04 | 0.08 | 0.16 | 0.32 | 0.64 | 1.28 |
| μ [h$^{-1}$] | 0 | 0 | 0 | 0 | 0 | 0 | 0 | 0 | 0 |
| $t_d$ [h] | 0 | 0 | 0 | 0 | 0 | 0 | 0 | 0 | 0 |

Figure 4:
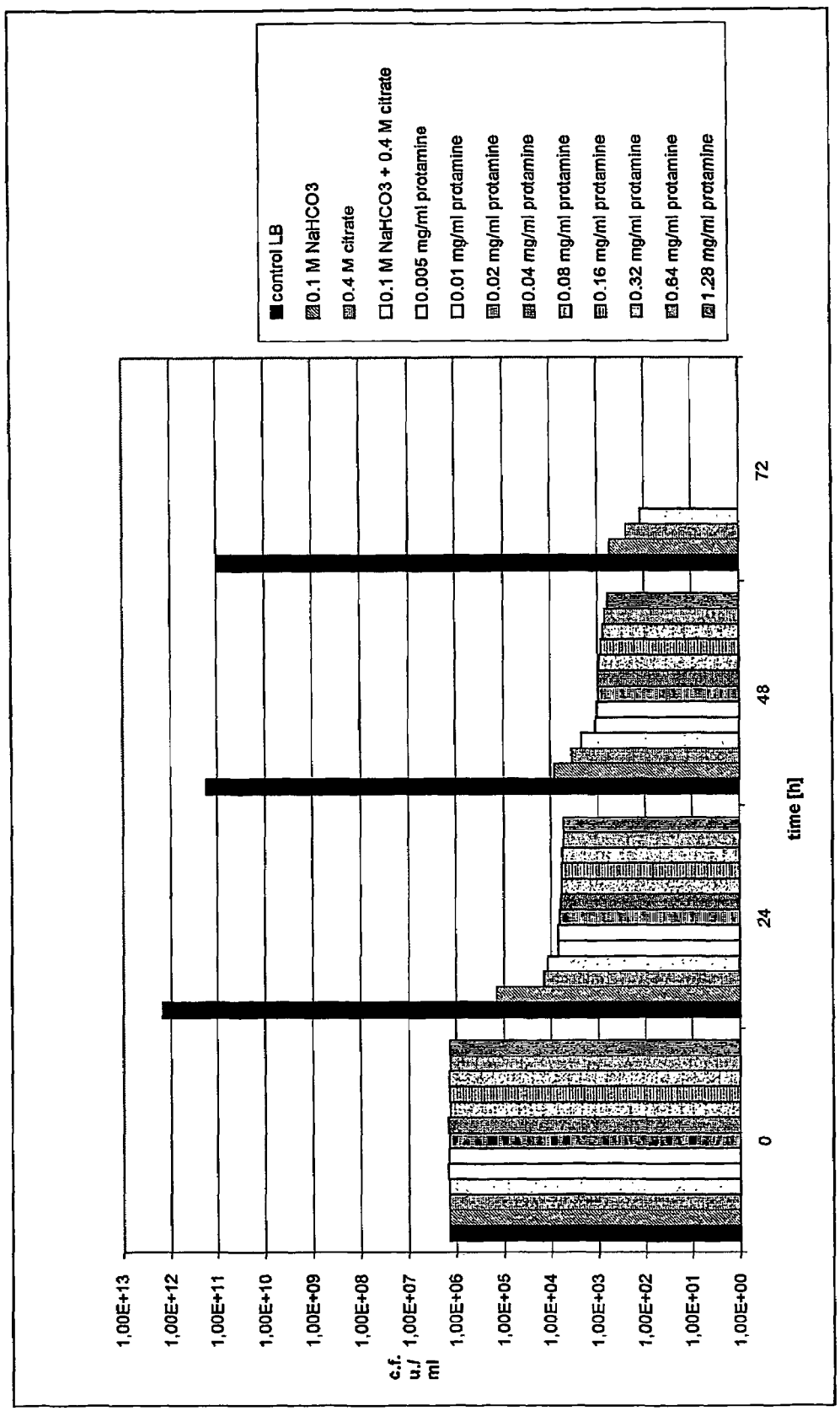
FIG. 4 shows the effect of single components (citrate or bicarbonate) of the composition at a pH of 8.0 as well as in combination and in the presence of different concentrations of protamine on the growth of *Micrococcus luteus* DSM 348.

The results are shown in FIG. 4.

The invention claimed is:

1. An isolated DNA molecule comprising a nucleotide sequence that encodes a protamine polypeptide, wherein the nucleotide sequence is as set out in SEQ IED NO. 32.

2. An isolated DNA molecule providing an expression cassette capable of directing the expression of a protamine polypeptide in a suitable host, wherein said expression cassette comprises from 5' to 3':

(a) a promoter capable of expressing a downstream coding sequence in a suitable host;

(b) a DNA sequence coding for the expression of the protamine polypeptide; and (c) a 3' termination sequence, wherein the DNA sequence (b) is as set out in SEQ ID NO. 32.

3. An isolated DNA molecule according to claim 1, wherein the coding nucleotide sequence is a cDNA, genomic or manufactured DNA sequence.

4. An isolated DNA molecule according to claim 2, wherein the coding nucleotide sequence is fused with a suitable signal peptide encoding sequence.

5. An isolated DNA molecule according to claim 2, wherein the promoter, or the coding nucleotide sequence, or the promoter and the coding nucleotide sequence, are selected to ensure expression in an eucaryotic host.

6. An isolated DNA molecule according to claim 2, wherein the promoter, or the coding nucleotide sequence, or the promoter and the coding nucleic acid sequence, are selected to ensure expression in a procaryotic host.

7. An isolated DNA molecule according to claim 5, wherein the promoter is an inducible promoter.

8. A plasmid or vector system comprising one or more DNA molecules according to claim 1.

9. A procaryotic or eucaryotic host cell, tissue or microorganism transformed or transfected with the DNA molecule according to claim 2 in a manner enabling said host cell, tissue or microorganism to express protamine polypeptide.

10. The procaryotic or eucaryotic host cell, tissue or microorganism according to claim 9 selected from the group consisting of bacteria, fungi including yeast, insect, animal and plant cells, and tissues.

11. The procaryotic or eucaryotic host cell, tissue or microorganism according to claim 10 that is a procaryotic host cell, wherein the procaryotic host cell is a bacterium selected from the group consisting of proteobacteria including members of the alpha, beta, gamma, delta and epsilon subdivision, gram-positive bacteria including *Actinomycetes, Firmicutes, Clostridium* and relatives, *flavobacteria, cyanobacteria, green sulfur bacteria, green non-sulfur bacteria,* and *archaea.*

12. The procaryotic or eucaryotic host cell, tissue or microorganism according to claim 11, wherein the procaryotic host cell belongs to the group of proteobacteria selected from the group consisting of *Agrobacterium, Rhodospirillum, Rhodopseudomonas, Rhodobacter, Rhodomi-crobium, Rhodopila, Rhizobium, Nitrobacter, Aquaspi-rillum, Hyphomicrobium, Acetobacter, Beijerinckia, Paracoccus, Pseudomonas,* ammonia-oxidizing bacteria such as *Nitrosomonas, Enterobacteriaceae, Myxobacteria* such as *Myxococcus.*

13. The procaryotic or eucaryotic host cell, tissue or microorganism according to claim 11, wherein the procaryotic host cell belongs to the group of gram-positive bacteria selected from the group consisting of *Actinomycetes* and *Firmicutes* including *Clostridium* and relatives such as *Bacillus* and *Lactococcus*.

14. The procaryotic or eucaryotic host cell, tissue or microorganism according to claim 11, wherein the procaryotic host cell belongs to the group of *flavobacteria* selected from the group consisting of *Bacteroides, Cytophaga* and *Flavobacterium*.

15. The procaryotic or eucaryotic host cell, tissue or microorganism according to claim 11, wherein the procaryotic host cell belongs to the group of cyanobacteria selected from the group consisting of *Chlorococcales* including *Synechocystis* and *Synechococcus*.

16. The procaryotic or eucaryotic host cell, tissue or microorganism according to claim 11, wherein the procaryotic host cell belongs to the groups of green sulfur bacteria or green non-sulfur bacteria selected from the group consisting of *Chlorobium* and *Chloroflexaceae* including *Chloroflexus*.

17. The procaryotic or eucaryotic host cell, tissue or microorganism according to claim 11, wherein the procaryotic host cell belongs to the group of archaea selected from *Halobacteriaceae* including *Halobacterium*.

18. The procaryotic or eucaryotic host cell, tissue or microorganism according to claim 10 that is an eucaryotic host cell or microorganism that is a fungi including yeast selected from the group consisting of *Ascomycota* including Saccharomycetes including Pichia and Saccharomyces, and anamorphic Ascomycota including Aspergillus.

19. The procaryotic or eucaryotic host cell, tissue or microorganism according to claim 10 that is an eucaryotic host cell that is an insect cell selected from the group consisting of SF9, SF21, Trychplusiani and MB21.

20. The procaryotic or eucaryotic host cell, tissue or microorganism according to claim 10 that is an eucaryotic host cell that is an animal cell selected from the group consisting of Baby Hamster Kidney (BHK) cells, Chinese Hamster Ovarian (CHO) cells, Human Embryonic Kidney (HEK) cells and COS cells.

21. The prokaryotic or eucaryotic host cell, tissue or microorganism according to claim 10 that is an eucaryotic host cell that is a plant cell selected from the group consisting of eukaryotic alga, embryophytes comprising *Bryophyta, Pteridophyta* and Spermatophyta including *Gymnospermae* and *Angiospermae,* wherein *Angiospermae* include *Magnoliopsida, Rosopsida,* and *Liliopsida*.

22. A method of transforming or transfecting a procaryotic or eucaryotic host cell, tissue or microorganism with a DNA molecule in a manner enabling said host cell, &eed-tissue or microorganism to express a protamine polypeptide, wherein the DNA molecule provides an expression cassette capable of directing the expression of the protamine polypeptide in the host cell, wherein said expression cassette comprises from 5' to 3'
   (a) a promoter capable of expressing a downstream coding sequence in a suitable host;
   (b) a DNA sequence coding for the expression of the protamine polypeptide; and
   (c) a 3' termination sequence, wherein the DNA sequence (b) is as set out in SEQ ID NO. 32, in order to yield transformants or transfectants capable of expressing the protamine polypeptide, the method comprising the steps of:
   (i) providing the procaryotic or eucaryotic host cell, tissue or microorganism; and
   (ii) performing a transformation or transfection of said host cell, tissue or microorganism with the DNA molecule according claim 2.

23. A transformed or transfected host cell, tissue or microorganism represented by or regenerated from transformants or transfectants yielded according to claim 22.

24. A method for the production of a protamine polypeptide, comprising the steps of:
   (a) culturing a transformed or transfected host cell, tissue or microorganism represented by or regenerated from transformants or transfectants in culture medium under suitable conditions allowing production of said polypeptide within said host; and, optionally,
   (b) isolating said polypeptide from said host or from the culture medium, wherein the transformants or transfectants are yielded by transforming or transfecting a procaryotic or eucaryotic host cell, tissue or microorganism with a DNA molecule in a manner enabling said host cell, tissue or microorganism to express said protamine polypeptide, wherein the DNA molecule provides an expression cassette capable of directing the expression of the protamine polypeptide in the host cell, wherein said expression cassette comprises from 5' to 3'
   (i) a promoter capable of expressing a downstream coding sequence in a suitable host;
   (ii) a DNA sequence coding for the expression of said protamine polypeptide; and
   (iii) a 3' termination sequence, wherein the DNA sequence (b) is as set out in SEQ ID NO. 32, in order to yield transformants or transfectants capable of expressing the protamine polypeptide, wherein the transformants are yielded by
   (1) providing the prokaryotic or eucaryotic host cell, tissue or microorganism; and
   (2) performing a transformation or transfection of said host cell, tissue or microorganism with the DNA molecule according claim 2.

25. A method according to claim 24, wherein said transformed or transfected host cell is selected from prokaryotes, and wherein said polypeptide is isolated after induction of a log phase culture with a suitable inducing agent.

26. A method according to claim 25, wherein said polypeptide or functional fragment is isolated until said host cell re-enters log phase.

27. A procaryotic or eucaryotic host cell, tissue or microorganism transformed or transfected with the plasmid or vector system according to claim 8 in a manner enabling said host cell, tissue or microorganism to express a protamine polypeptide.

28. The procaryotic or eucaryotic host cell, tissue or microorganism according to claim 12, wherein the procaryotic host cell belongs to the group of proteobacteria selected from the group consisting of *Rhodopseudomonas, Pseudomonas* and *Escherichia*.

29. The procaryotic or eucaryotic host cell, tissue or microorganism according to claim 28, wherein the procaryotic host cell belongs to the group of proteobacteria selected from the group consisting of *Rhodopseudomonas palustris, Pseudomonas fluorescens,* and *Escherichia coli*.

30. The prokaryotic or eucaryotic host cell, tissue or microorganism according to claim 13, wherein the procaryotic host cell belongs to the group of gram-positive bacteria selected from the group consisting of *Bacillus subtilis* and *Lactococcus lactis*.

31. The prokaryotic or eucaryotic host cell, tissue or microorganism according to claim 14, wherein the procaryotic host cell belongs to the group of flavobacteria including Flavobacterium.

32. The procaryotic or eucaryotic host cell, tissue or microorganism according to claim 15, wherein the procaryotic host cell belongs to the group of cyanobacteria selected from the group consisting of *Synechocystis* sp. and *Synechococcus* sp. PS717.

33. The procaryotic or eucaryotic host cell, tissue or microorganism according to claim 16, wherein the procaryotic host cell belongs to the groups of green sulfur bacteria or green non-sulfur bacteria selected from the group consisting of *Chlorobium limicola f thiosulfatophilum* and *Chloroflexus aurantiacus*.

34. The procaryotic or eucaryotic host cell, tissue or who microorganism according to claim 17, wherein the procaryotic host cell belongs are *Halobacterium salinarum*.

35. The procaryotic or eucaryotic host cell, tissue or microorganism according to claim 18, wherein the eucaryotic host cell is selected from the group consisting of *Saccharomyces cerevisiae* and *Aspergillus niger*.

36. The procaryotic or eucaryotic host cell, tissue or microorganism according to claim 20, wherein the eucaryotic host cell is an animal cell selected from the group consisting of NIH 3T3 and 293 cells.

37. A method of transforming or transfecting a prokaryotic or eucaryotic host cell, tissue or microorganism transformed or transfected with a DNA molecule in a manner enabling said host cell, tissue or microorganism to express a protamine polypeptide, wherein the DNA molecule provides an expression cassette capable of directing the expression of the protamine polypeptide in the host cell, wherein said expression cassette comprises from 5' to 3'
   (a) a promoter capable of expressing a downstream coding sequence in a suitable host;
   (b) a DNA sequence coding for the expression of the protamine polypeptide; and
   (c) a 3' termination sequence, wherein the DNA sequence (b) is as set out in SEQ ID NO. 32, in order to yield transformants or transfectants capable of expressing the protamine polypeptide, the method comprising the steps of:
   (i) providing the prokaryotic or eucaryotic host cell, tissue or whole microorganism; and
   (ii) performing a transformation or transfection of said host cell, tissue or microorganism with the plasmid or vector system according to claim 8.

38. A transformed or transfected host cell, tissue or microorganism represented by or regenerated from transformants or transfectants yielded according to claim 37.

39. A method for the production of a protamine polypeptide, comprising the steps of:
   (a) culturing a transformed or transfected host cell, tissue or whole microorganism represented by or regenerated from transformants or transfectants in culture medium under suitable conditions allowing production of said polypeptide within said host; and, optionally,
   (b) isolating said polypeptide from said host or from the culture medium, wherein the transformants or transfectants are yielded by transforming or transfecting a procaryotic or eucaryotic host cell, tissue or 1 microorganism with a DNA molecule in a manner enabling said host cell, tissue or microorganism to express said protamine polypeptide, wherein the DNA molecule provides an expression cassette capable of directing the expression of the protamine polypeptide in the host cell, wherein said expression cassette comprises from 5' to 3'
   (i) a promoter capable of expressing a downstream coding sequence in a suitable host;
   (ii) a DNA sequence coding for the expression of said protamine polypeptide; and
   (iii) a 3' termination sequence, wherein the DNA sequence (b) is as set out in SEQ ID NO. 32, in order to yield transformants or transfectants capable of expressing the protamine polypeptide, wherein the transformants are yielded by
   (1) providing the prokaryotic or eucaryotic host cell, tissue or microorganism; and
   (2) performing a transformation or transfection of said host cell, tissue or microorganism with the plasmid or vector system according to claim 8.

40. A method according to claim 39, wherein said transformed or transfected host cell is selected from prokaryotes, and wherein said polypeptideis isolated after induction of a log phase culture with a suitable inducing agent.

41. A method according to claim 40, wherein said polypeptideis isolated until said host cell re-enters log phase.

42. A method according to claim 40, wherein said transformed or transfected host cell is selected from the group consisting of *Rhodopseudomonas palustris, Pseudomonas fluorescens,* and *Escherichia coli.*

43. A method according to claim 25, wherein said transformed or transfected host cell is selected from the group consisting of *Rhodopseudomonas palustris, Pseudomonas fluorescens,* and *Escherichia coli.*

* * * * *